(12) United States Patent
Wright et al.

(10) Patent No.: US 8,095,203 B2
(45) Date of Patent: Jan. 10, 2012

(54) DATA PROCESSING FOR REAL-TIME TRACKING OF A TARGET IN RADIATION THERAPY

(75) Inventors: J. Nelson Wright, Mercer Island, WA (US); Steven C. Dimmer, Bellevue, WA (US); Stephen C. Phillips, Woodinville, WA (US); Ryan K. Seghers, Kirkland, WA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 1201 days.

(21) Appl. No.: 11/190,205

(22) Filed: Jul. 25, 2005

(65) Prior Publication Data

US 2006/0100509 A1    May 11, 2006

Related U.S. Application Data

(60) Provisional application No. 60/590,693, filed on Jul. 23, 2004.

(51) Int. Cl.
*A61B 5/05* (2006.01)
(52) U.S. Cl. ......... 600/426; 600/407; 600/437; 600/410
(58) Field of Classification Search .................. 600/407, 600/409, 410, 426–428, 473–478
See application file for complete search history.

(56) References Cited

U.S. PATENT DOCUMENTS

| | | | |
|---|---|---|---|
| 3,967,161 A | 6/1976 | Lichtblau | |
| 4,023,167 A | 5/1977 | Wahlstrom | |
| 4,114,601 A | 9/1978 | Abels | |
| 4,123,749 A | 10/1978 | Hartmann et al. | |
| 4,127,110 A | 11/1978 | Bullara | |
| 4,160,971 A | 7/1979 | Jones et al. | |
| 4,222,374 A | 9/1980 | Sampson et al. | |
| 4,260,990 A | 4/1981 | Lichtblau | |
| 4,393,872 A | 7/1983 | Reznik et al. | |
| 4,618,822 A | 10/1986 | Hansen | |
| 4,633,250 A | 12/1986 | Anderson | |
| 4,643,196 A | 2/1987 | Tanaka et al. | |
| 4,696,287 A | 9/1987 | Hortmann et al. | |
| 4,795,995 A | 1/1989 | Eccleston | |
| 4,799,495 A | 1/1989 | Hawkins | |
| 4,909,789 A | 3/1990 | Taguchi et al. | |
| 4,936,823 A | 6/1990 | Colvin et al. | |
| 4,945,914 A * | 8/1990 | Allen ........................... | 600/426 |

(Continued)

FOREIGN PATENT DOCUMENTS

DE    19914455 A1    10/2000

(Continued)

OTHER PUBLICATIONS

U.S. Appl. No. 60/590,503, filed Jul. 23, 2004, Wright et al.

(Continued)

*Primary Examiner* — Tse Chen
*Assistant Examiner* — Joel F Brutus
(74) *Attorney, Agent, or Firm* — Perkins Coie LLP

(57) ABSTRACT

A facility for processing data is described. The facility receives a stream of digital location indications, each location indication identifying a location of a patient while undergoing radiation therapy. In response to each location indication of the string, in substantially real-time relative to the receipt of the position indication, the facility performs an action responsive to the location indication.

54 Claims, 23 Drawing Sheets

U.S. PATENT DOCUMENTS

| | | | |
|---|---|---|---|
| 4,994,079 A | 2/1991 | Genese | |
| 5,031,634 A | 7/1991 | Simon | |
| 5,062,847 A | 11/1991 | Barnes | |
| 5,095,224 A | 3/1992 | Renger | |
| 5,099,845 A | 3/1992 | Besz et al. | |
| 5,107,862 A | 4/1992 | Fabian et al. | |
| 5,142,292 A | 8/1992 | Chang | |
| 5,170,055 A | 12/1992 | Carroll et al. | |
| 5,325,873 A | 7/1994 | Hirschi et al. | |
| 5,353,804 A | 10/1994 | Kornberg et al. | |
| 5,409,004 A | 4/1995 | Sloan | |
| 5,423,334 A | 6/1995 | Jordan | |
| 5,425,367 A | 6/1995 | Shapiro | |
| 5,425,382 A | 6/1995 | Golden et al. | |
| 5,446,548 A * | 8/1995 | Gerig et al. | 356/620 |
| 5,509,900 A | 4/1996 | Kirkman | |
| 5,528,651 A | 6/1996 | Leksell | |
| 5,626,630 A | 5/1997 | Markowitz et al. | |
| 5,638,819 A | 6/1997 | Manwaring et al. | |
| 5,651,043 A | 7/1997 | Tsuyuki et al. | |
| 5,680,106 A | 10/1997 | Schrott | |
| 5,697,384 A | 12/1997 | Miyawaki et al. | |
| 5,707,362 A | 1/1998 | Yoon | |
| 5,707,390 A | 1/1998 | Bonutti | |
| 5,711,299 A | 1/1998 | Manwaring et al. | |
| 5,727,552 A | 3/1998 | Ryan | |
| 5,735,795 A | 4/1998 | Young et al. | |
| 5,748,767 A | 5/1998 | Raab | |
| 5,754,623 A | 5/1998 | Seki et al. | |
| 5,757,881 A | 5/1998 | Hughes | |
| 5,764,052 A | 6/1998 | Renger | |
| 5,769,861 A | 6/1998 | Vilsmeier | |
| 5,810,851 A | 9/1998 | Yoon | |
| 5,815,076 A | 9/1998 | Herring | |
| 5,840,148 A | 11/1998 | Campbell | |
| 5,868,673 A | 2/1999 | Vesely | |
| 5,879,297 A | 3/1999 | Haynor et al. | |
| 5,910,144 A | 6/1999 | Hayashi | |
| 5,928,137 A | 7/1999 | Green et al. | |
| 5,951,481 A | 9/1999 | Evans | |
| 5,957,934 A | 9/1999 | Rapoport et al. | |
| 5,989,265 A | 11/1999 | Bouquet De La Joliniere et al. | |
| 6,026,818 A | 2/2000 | Blair | |
| 6,059,734 A | 5/2000 | Yoon | |
| 6,061,644 A | 5/2000 | Leis | |
| 6,067,465 A | 5/2000 | Foo | |
| 6,076,008 A | 6/2000 | Bucholz | |
| 6,081,238 A | 6/2000 | Alicot | |
| 6,082,366 A | 7/2000 | Andra et al. | |
| 6,144,875 A | 11/2000 | Schweikard et al. | |
| 6,161,009 A * | 12/2000 | Skurdal et al. | 455/423 |
| 6,198,963 B1 | 3/2001 | Haim et al. | |
| 6,246,900 B1 | 6/2001 | Cosman et al. | |
| 6,307,473 B1 | 10/2001 | Zampini et al. | |
| 6,353,655 B1 | 3/2002 | Siochi | |
| 6,359,959 B1 | 3/2002 | Butler et al. | |
| 6,363,940 B1 | 4/2002 | Krag | |
| 6,371,379 B1 | 4/2002 | Dames | |
| 6,377,162 B1 | 4/2002 | Delestienne et al. | |
| 6,381,485 B1 | 4/2002 | Hunter et al. | |
| 6,385,286 B1 | 5/2002 | Fitchard et al. | |
| 6,385,288 B1 | 5/2002 | Kanematsu | |
| 6,393,096 B1 * | 5/2002 | Carol et al. | 378/65 |
| 6,405,072 B1 | 6/2002 | Cosman | |
| 6,416,520 B1 | 7/2002 | Kynast et al. | |
| 6,501,981 B1 | 12/2002 | Schweikard et al. | |
| 6,510,199 B1 | 1/2003 | Hughes et al. | |
| 6,526,415 B2 | 2/2003 | Smith et al. | |
| 6,535,756 B1 | 3/2003 | Simon et al. | |
| 6,650,930 B2 | 11/2003 | Ding et al. | |
| 6,662,036 B2 | 12/2003 | Cosman | |
| 6,675,810 B2 | 1/2004 | Krag | |
| 6,698,433 B2 | 3/2004 | Krag | |
| 6,812,842 B2 | 11/2004 | Dimmer | |
| 6,822,570 B2 | 11/2004 | Dimmer et al. | |
| 6,838,990 B2 | 1/2005 | Dimmer | |
| 6,882,947 B2 | 4/2005 | Levin | |
| 6,918,919 B2 | 7/2005 | Krag | |
| 6,934,356 B1 | 8/2005 | Satheesan et al. | |
| 6,937,696 B1 | 8/2005 | Mostafavi | |
| 6,977,504 B2 | 12/2005 | Wright et al. | |
| 6,993,112 B2 | 1/2006 | Hesse et al. | |
| 6,999,555 B2 | 2/2006 | Morf et al. | |
| 7,026,927 B2 | 4/2006 | Wright et al. | |
| 7,027,707 B2 | 4/2006 | Imaki et al. | |
| 7,142,905 B2 | 11/2006 | Slayton et al. | |
| 7,154,991 B2 | 12/2006 | Earnst et al. | |
| 7,206,626 B2 | 4/2007 | Quaid, III | |
| 7,206,627 B2 | 4/2007 | Abovitz et al. | |
| 7,213,009 B2 | 5/2007 | Pestotnik et al. | |
| 7,221,733 B1 | 5/2007 | Takai et al. | |
| 7,289,599 B2 | 10/2007 | Seppi et al. | |
| 7,289,839 B2 | 10/2007 | Dimmer et al. | |
| 7,447,643 B1 | 11/2008 | Olson et al. | |
| 7,606,405 B2 | 10/2009 | Sawyer et al. | |
| 2002/0049362 A1 | 4/2002 | Ding | |
| 2002/0065461 A1* | 5/2002 | Cosman | 600/426 |
| 2002/0165443 A1 | 11/2002 | Mori | |
| 2002/0188194 A1 | 12/2002 | Cosman | |
| 2002/0193685 A1* | 12/2002 | Mate et al. | 600/424 |
| 2003/0002621 A1 | 1/2003 | Hughes et al. | |
| 2003/0023161 A1 | 1/2003 | Govari et al. | |
| 2003/0052785 A1 | 3/2003 | Gisselberg | |
| 2003/0088178 A1 | 5/2003 | Owens et al. | |
| 2003/0125616 A1 | 7/2003 | Black et al. | |
| 2003/0153829 A1 | 8/2003 | Sarin et al. | |
| 2003/0192557 A1 | 10/2003 | Krag | |
| 2003/0206610 A1 | 11/2003 | Collins | |
| 2003/0206614 A1* | 11/2003 | Kendrick et al. | 378/205 |
| 2004/0019274 A1 | 1/2004 | Galloway et al. | |
| 2004/0068182 A1 | 4/2004 | Misra | |
| 2004/0096033 A1 | 5/2004 | Seppi et al. | |
| 2004/0116804 A1 | 6/2004 | Mostafavi | |
| 2004/0122311 A1 | 6/2004 | Cosman | |
| 2004/0122608 A1 | 6/2004 | Levin | |
| 2004/0125916 A1 | 7/2004 | Herron et al. | |
| 2004/0127787 A1 | 7/2004 | Dimmer et al. | |
| 2004/0133101 A1 | 7/2004 | Mate et al. | |
| 2004/0138555 A1 | 7/2004 | Krag | |
| 2004/0158146 A1 | 8/2004 | Mate et al. | |
| 2004/0176931 A1 | 9/2004 | Wright et al. | |
| 2005/0059884 A1 | 3/2005 | Krag | |
| 2005/0059887 A1 | 3/2005 | Mostafavi et al. | |
| 2005/0077459 A1 | 4/2005 | Engler et al. | |
| 2005/0085710 A1 | 4/2005 | Earnst et al. | |
| 2005/0151649 A1 | 7/2005 | Wright et al. | |
| 2005/0152495 A1 | 7/2005 | Hesse | |
| 2005/0154280 A1 | 7/2005 | Wright et al. | |
| 2005/0154283 A1 | 7/2005 | Wright et al. | |
| 2005/0154284 A1 | 7/2005 | Wright et al. | |
| 2005/0154293 A1 | 7/2005 | Gisselberg | |
| 2005/0195084 A1 | 9/2005 | Dimmer | |
| 2005/0234332 A1 | 10/2005 | Murphy | |
| 2005/0261570 A1 | 11/2005 | Mate et al. | |
| 2006/0052694 A1 | 3/2006 | Phillips et al. | |
| 2006/0058648 A1 | 3/2006 | Meier et al. | |
| 2006/0063999 A1 | 3/2006 | Herron et al. | |
| 2006/0074301 A1 | 4/2006 | Meier et al. | |
| 2006/0074302 A1 | 4/2006 | Meier et al. | |
| 2006/0078086 A1 | 4/2006 | Riley et al. | |
| 2006/0079764 A1 | 4/2006 | Wright et al. | |
| 2007/0161884 A1 | 7/2007 | Black et al. | |

FOREIGN PATENT DOCUMENTS

| | | |
|---|---|---|
| EP | 0531081 A1 | 1/1992 |
| FR | 26335259 | 2/1990 |
| FR | 2686499 | 7/1993 |
| JP | 8-166446 | 6/1996 |
| WO | WO-95/25475 | 9/1995 |
| WO | WO-97/12553 | 4/1997 |
| WO | WO-98/30166 | 7/1998 |
| WO | WO-98/38908 | 9/1998 |
| WO | WO-98/40026 A | 9/1998 |
| WO | WO-99/30182 | 6/1999 |
| WO | WO-99/33406 | 7/1999 |
| WO | WO-99/40869 | 8/1999 |
| WO | WO-99/58044 | 11/1999 |

| WO | WO-99/58065 | 11/1999 |
| WO | WO-00/38579 | 7/2000 |
| WO | WO-00/51514 | 9/2000 |
| WO | WO-00/53115 | 9/2000 |
| WO | WO-00/65989 A | 11/2000 |
| WO | WO-02/39917 | 5/2002 |
| WO | WO-02/39918 | 5/2002 |
| WO | WO-0239918 | 5/2002 |

OTHER PUBLICATIONS

U.S. Appl. No. 60/590,693, filed Jul. 23, 2004, Wright et al.
U.S. Appl. No. 60/590,697, filed Jul. 23, 2004, Phillips et al.
U.S. Appl. No. 60/590,699, filed Jul. 23, 2004, Herron et al.
U.S. Appl. No. 10/416,827, filed Nov. 17, 2000, Krag.

* cited by examiner

TRACKING DATA

| StartDateTime | EndDateTime | Number Of Target Points | Number Of Beacon Points |
|---|---|---|---|
| | | int | int |
| 2004-05-25T14:47:44.8906250-07:00 | 2004-05-25T14:48:56.5312500-07:00 | 708 | 705 |

Target Data

| X | Y | Z | Confiden | ResultCode | Psi | Phi | Theta | MeasurementDateTime | DeltaTime |
|---|---|---|---|---|---|---|---|---|---|
| | | | | | | | | | double |
| -0.431374218 | -0.067678053 | -0.381511265 | 0 | NotAllBeac | 90.0000025 | 0 | 0 | 2004-05-25T14:47:45.2628750-07:00 | 0 |
| -0.431283931 | -0.067798719 | -0.378818271 | 0 | NotAllBeac | 90.0000025 | 0 | 0 | 2004-05-25T14:47:45.2628750-07:00 | 0 |
| -0.431518817 | -0.067916224 | -0.378237521 | 0 | Okay | 90.0000025 | 0 | 0 | 2004-05-25T14:47:45.3438750-07:00 | 0.37225 |
| -0.431518817 | -0.067916224 | -0.378237521 | 0 | Okay | 90.0000025 | 0 | 0 | 2004-05-25T14:47:45.4558750-07:00 | 0.45325 |
| -0.431097335 | -0.066685713 | -0.379974794 | 0 | Okay | 90.0000025 | 0 | 0 | 2004-05-25T14:47:45.4558750-07:00 | 0.56525 |
| -0.431153528 | -0.066846079 | -0.381337902 | 0 | Okay | 90.0000025 | 0 | 0 | 2004-05-25T14:47:45.5468750-07:00 | 0.56525 |
| -0.431286869 | -0.066407504 | -0.381912416 | 0 | Okay | 90.0000025 | 0 | 0 | 2004-05-25T14:47:45.6278750-07:00 | 0.65625 |
| -0.430794488 | -0.067037691 | -0.381474649 | 0 | Okay | 90.0000025 | 0 | 0 | 2004-05-25T14:47:45.7798750-07:00 | 0.73725 |
| -0.430981242 | -0.066643381 | -0.381864133 | 0 | Okay | 90.0000025 | 0 | 0 | 2004-05-25T14:47:45.8608750-07:00 | 0.88925 |
| -0.431201219 | -0.067218443 | -0.382348945 | 0 | Okay | 90.0000025 | 0 | 0 | 2004-05-25T14:47:45.9418750-07:00 | 0.97025 |
| -0.431454799 | -0.066539192 | -0.383149773 | 0 | Okay | 90.0000025 | 0 | 0 | 2004-05-25T14:47:46.0638750-07:00 | 1.05125 |
| -0.431201219 | -0.067218443 | | 0 | Okay | 90.0000025 | 0 | 0 | 2004-05-25T14:47:46.1448750-07:00 | 1.17325 |
| -0.429863363 | -0.065858336 | -0.384109138 | 0 | Okay | 90.0000025 | 0 | 0 | 2004-05-25T14:47:46.2258750-07:00 | 1.24525 |
| | | | | | | | | | 1.33525 |

*Fig. 6*

DATA PROCESSING FOR REAL-TIME TRACKING OF A TARGET IN RADIATION THERAPY

CROSS-REFERENCE TO RELATED APPLICATIONS

This application claims the benefit of U.S. patent application Ser. No. 60/590,693 filed Jul. 23, 2004, which is hereby incorporated by reference in its entirety.

TECHNICAL FIELD

The present invention is directed to the field of software systems for processing real-time information.

BACKGROUND

Radiation therapy can be used to treat localized cancer. In a typical application, a radiation delivery system has an ionizing radiation device mounted to a movable gantry. The radiation delivery system controls the motion of the radiation device to direct an ionizing radiation beam to a specific point in space commonly referred to as the "machine isocenter."

One aspect of radiation therapy is positioning a patient so that the patient's tumor is located at the machine isocenter during treatment. Conventional patient positioning systems use various technologies to locate the tumor, including optically locating visual markers applied to the patient's skin, or using X-ray imaging to locate metal fiducials subcutaneously implanted in the patient. Conventional patient positioning systems are typically used only to align patients in preparation for the delivery of radiation energy.

To ensure that radiation energy is delivered to a patient's tumor as planned, though, it would be useful to provide patient location information during the delivery of radiation energy. It can be difficult to successfully apply conventional approaches to patient tracking to provide patient location information during the delivery of radiation, however.

Using conventional X-ray based tracking techniques, each tracking measurement exposes the patient to an additional dose of X-ray imaging radiation. Were the use of X-ray based tracking expanded to operate throughout the course of radiation therapy, the patient would be exposed to potentially harmful levels of X-ray imaging radiation. Additionally, in some implementations, the delivery of energy during radiation therapy can interrupt the efficacy of X-ray based tracking techniques. For instance, the presence of radiation therapy radiation may interfere with the sensing of imaging radiation. As another example, the presence of the X-ray imaging emitter and/or sensor may physically interrupt the radiation treatment energy beam.

It can also be difficult to successfully apply conventional optical tracking techniques during the delivery of radiation. Here too, the presence of optical tracking sensors may interrupt the radiation treatment energy beam. Conversely, radiation treatment equipment may intervene between the patient and the optical tracking sensors, blocking their view of the patient. Also, as optical tracking techniques typically rely on 2-dimensional tracking of the exterior surface of the patient's body, their accuracy depends on the consistency of such factors as the shape of the exterior surface of the patient's body, and the location of the tumor relative to the locations of the visual markers. Because these factors are inherently variable, positioning data obtained using conventional optical tracking techniques can be inaccurate.

In view of the foregoing, a patient tracking system that provided useful patient tracking information during the delivery of radiation energy, and that promptly acted on such information, would have significant utility.

BRIEF DESCRIPTION OF THE DRAWINGS

FIG. 6 is a data structure diagram showing sample contents of the transcript stored by the patient tracking component and/or the database component.

Figure 1:
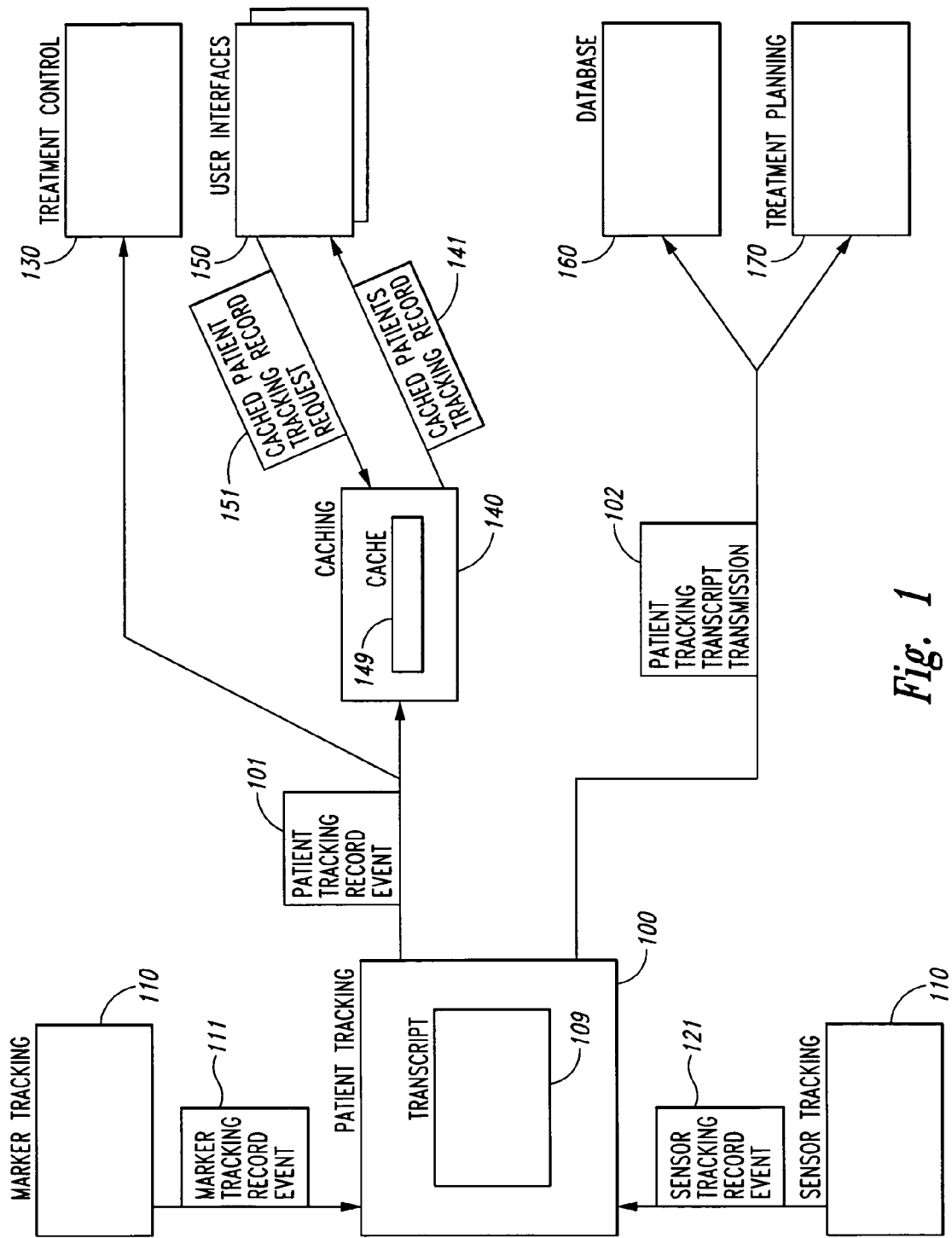
FIG. 1 is a data flow diagram showing a sample data flow used by the facility.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

Introduction

A software facility that performs real-time or near-real-time processing of patient tracking information during radiation therapy ("the facility") is described. As one illustrative example, some embodiments of the facility perform processing for patient tracking information generated in real-time or near-real-time by combining (1) information about the location of subcutaneously-implanted markers—such as passive magnetic transponders—relative to the sensor device used to locate the markers—such as an electromagnetic excitation and sensing array—with (2) information about the location of the sensor device relative to a machine isocenter to which radiation energy is delivered. One or more suitable, exemplary patient localization systems are described in the following, each of which is hereby incorporated by reference in its entirety: U.S. patent application Ser. No. 10/334,700, entitled PANEL-TYPE SENSOR/SOURCE ARRAY ASSEMBLY, filed Dec. 30, 2002; U.S. patent application Ser. No. 09/877,498, entitled GUIDED RADIATION THERAPY SYSTEM, filed Jun. 8, 2001; U.S. patent application Ser. No. 10/679,801, entitled METHOD AND SYSTEM FOR MARKER LOCALIZATION, filed Oct. 6, 2003; U.S. patent application Ser. No. 10/746,888, entitled IMPLANTABLE MARKER WITH WIRELESS SIGNAL TRANSMITTAL, filed Dec. 24, 2003; and U.S. patent application Ser. No. 10/749,478, entitled RECEIVER USED IN MARKER LOCALIZATION SENSING SYSTEM, filed Dec. 31, 2003.

In some embodiments, the facility uses a publish and subscribe scheme to promptly distribute patient tracking information for one or more real-time or near-real-time uses. For example, the facility may use the publish and subscribe scheme to distribute patient tracking information to a user interface component to display the patient's position for monitoring and/or to a treatment control component to adapt the treatment process to changes in the patient's position. In some embodiments, published patient tracking information is cached for lower-frequency uses of patient tracking information, and/or fixed-frequency uses of patient tracking information, such as displaying.

In some embodiments, the facility uses a bulk transfer scheme to less-frequently distribute patient tracking information, such as at the end of a session. The bulk transfer scheme may be used to distribute an entire session's patient tracking information, for example for non-volatile storage or use in planning a future treatment session.

By processing patient tracking information in some or all of the ways discussed above, the facility enables a variety of valuable uses of patient tracking information in connection with radiation therapy.

Processing Patient Tracking Information

FIG. 1 is a data flow diagram showing a sample data flow used by the facility. A patient tracking component 100 is responsible for generating patient tracking records each indicating the current location and/or orientation of a patient isocenter relative to a reference point, such as relative to a machine isocenter during radiation treatment. The patient tracking component subscribes to objects of at least two types: marker tracking record objects 111 published by a marker tracking component 110, and sensor tracking record objects 121, published by a sensor tracking component 120. The marker tracking record objects each contain a marker tracking record indicating the location and/or orientation of one or more markers implanted in the patient relative to the location and/or orientation of a marker sensor. Each sensor tracking record object contains a sensor tracking record indicating a position and/or orientation of the marker sensor device relative to the machine isocenter or other reference point. Using information contained in the marker tracking records and sensor tracking records that it receives, the patient tracking component computes the location and/or orientation of a patient isocenter—defined relative to the locations and/or orientation of the implanted markers—relative to the machine isocenter.

In some embodiments, the patient tracking component computes patient tracking records with no more than a maximum latency after the time of the underlying measurements, such as a maximum latency of 50 milliseconds, or a maximum latency of 200 milliseconds. In some embodiments, the patient tracking component generates patient tracking records at at least a minimum frequency, such as a minimum frequency of 20 hertz. Additional detail about the generation of patient tracking records is discussed in U.S. patent application Ser. No. 11/166,801 entitled SYSTEMS AND METHODS FOR REAL TIME TRACKING OF TARGETS IN RADIATION THERAPY AND OTHER MEDICAL APPLICATIONS, filed Jun. 24, 2005 and incorporated by reference in its entirety.

For each set of patient tracking information it computes, the patient tracking component stores a patient tracking record in a transcript 109 maintained by the patient tracking component, and publishes a patient tracking record object 101 containing the patient tracking record.

In some embodiments, the patient tracking component truncates, or "prunes" the contents of the patient tracking records included in the patient tracking record objects to reduce the communication resources needed to publish patient tracking record objects containing the pruned patient tracking records.

The patient tracking record objects published by the patient tracking component are subscribed to by components seeking real-time or near-real-time patient tracking information during the course of a radiation treatment session. For example, a treatment control component 130 may subscribe to the patient tracking record objects, and use the enclosed patient tracking records to control a variety of radiation treatment parameters. For example, in response to the patient tracking information, the treatment control component may alter the shape, direction, or intensity of the radiation energy being used to treat the patient; alter the location or orientation of the patient relative to the beam, such as by automatically moving the patient (or a table supporting the patient) or the beam; or switch the beam on or off, or pulse the beam. Additional details regarding the treatment control component's control of radiation treatment parameters are discussed in the patent applications incorporated by reference above.

In some embodiments, a caching component 140 also subscribes to the patient tracking record objects. The caching component 140 stores the patient tracking record contained in the most recently published patient tracking record object in a cache 149. Periodically, in some embodiments, one or more user interface components 150 send the caching component a cached patient tracking record request 151. (In some embodiments, however, some or all of the user interface components directly subscribe to the patient tracking record objects.) When the caching component receives a cached patient tracking record request from one of the user interface components, the caching component replies with a cached patient tracking record 141—i.e., the patient tracking record presently contained in the cache. As is discussed in additional detail in U.S. Patent Application No. 60/590,699, entitled USER INTERFACE FOR GUIDED RADIATION THERAPY, filed Jul. 23, 2004 and U.S. patent application Ser. No. 11/189,542 entitled USER INTERFACE FOR GUIDED RADIATION THERAPY, filed concurrently herewith, each of which is hereby incorporated by reference in its entirety, the user interfaces use the patient tracking records contained in the cached patient tracking record response to present a visual or other user interface reporting the patient tracking information, such as to radiation treatment attendants, in a graph or other form.

When a patient treatment session is completed, the patient tracking component sends a patient tracking transcript transmission 102, containing the transcript of the patient tracking records generated during the session. The patient tracking transcript transmission is sent to such recipients as a database 164 that stores the transcript in a non-volatile manner, and a treatment planning component 170 that uses the transcript to plan future treatment sessions for the same patient. Such adaptive treatment planning is discussed in additional detail in U.S. Patent Application Ser. No. 60/590,503, filed Jul. 23, 2004, entitled DYNAMIC/ADAPTIVE TREATMENT PLANNING FOR RADIATION THERAPY, and U.S. patent application Ser. No. 11/189,431, entitled DYNAMIC/ADAPTIVE TREATMENT PLANNING FOR RADIATION THERAPY, filed concurrently herewith, each of which is hereby incorporated by reference in its entirety.

The components shown in FIG. 1 may be implemented and may communicate in a variety of ways, including one or more discussed in U.S. Patent Application No. 60/590,697, entitled MODULAR SOFTWARE SYSTEM FOR GUIDED RADIATION THERAPY, filed on Jul. 23, 2004, and U.S. patent application Ser. No. 11/190,194, entitled MODULAR SOFTWARE SYSTEM FOR GUIDED RADIATION THERAPY, filed concurrently herewith, each of which is hereby incorporated by reference in its entirety.

Figure 2:
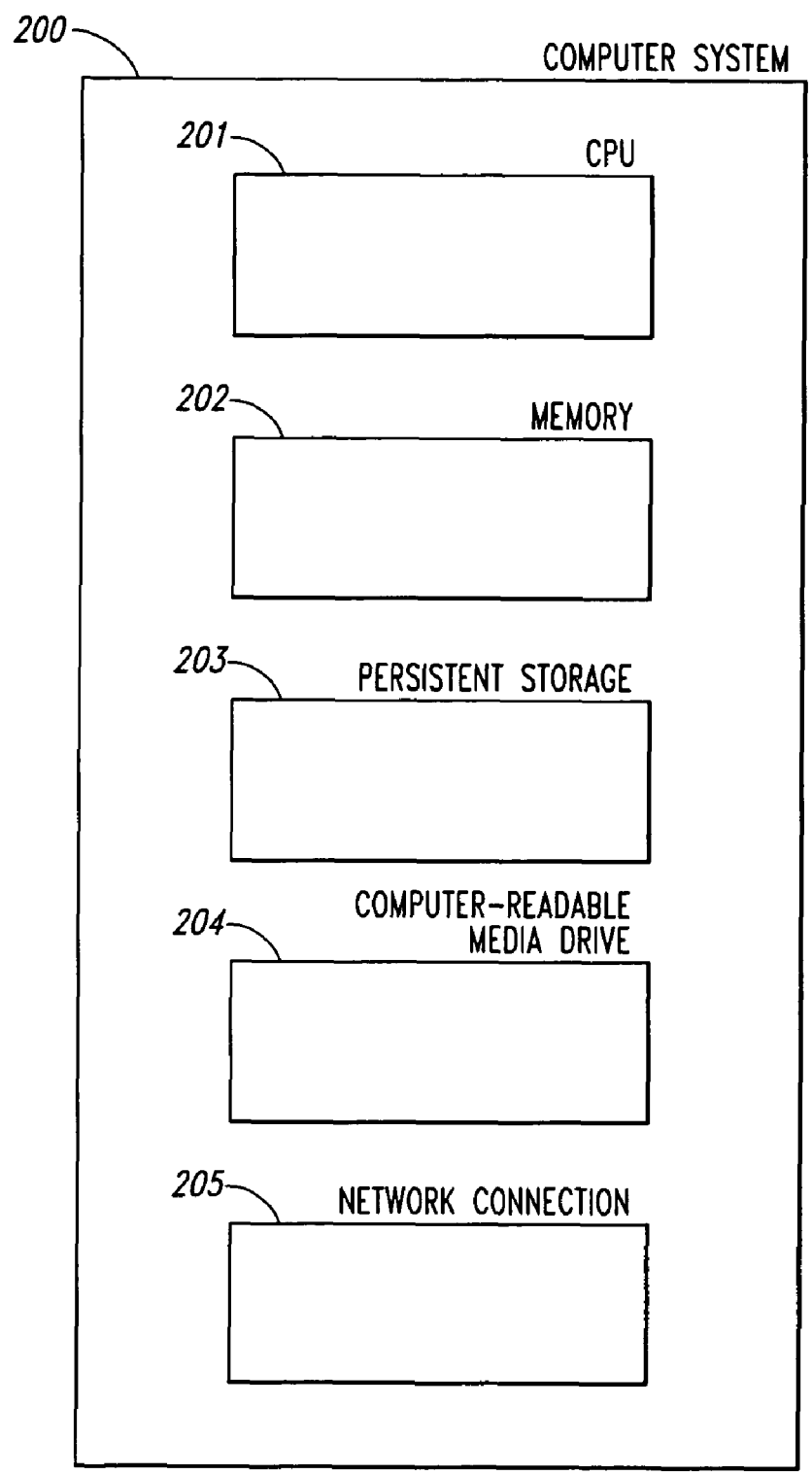
FIG. 2 is a block diagram showing some of the components typically incorporated in at least some of the computer systems and other devices on which the facility executes.

FIG. 2 is a block diagram showing some of the components typically incorporated in at least some of the computer systems and other devices on which the facility executes. These computer systems and devices 200 may include one or more central processing units ("CPUs") 201 for executing computer programs; a computer memory 202 for storing programs and data—including data structures—while they are being used; a persistent storage device 203, such as a hard drive, for persistently storing programs and data; a computer-readable media drive 104, such as a CD-ROM drive, for reading programs and data stored on a computer-readable medium; and a network connection 205 for connecting the computer system to other computer systems, such as via the Internet, to exchange programs and/or data—including data structures. While computer systems configured as described above are typically used to support the operation of the facility, one of ordinary skill in the art will appreciate that the facility may be implemented using devices of various types and configurations, and having various components.

Figure 3:
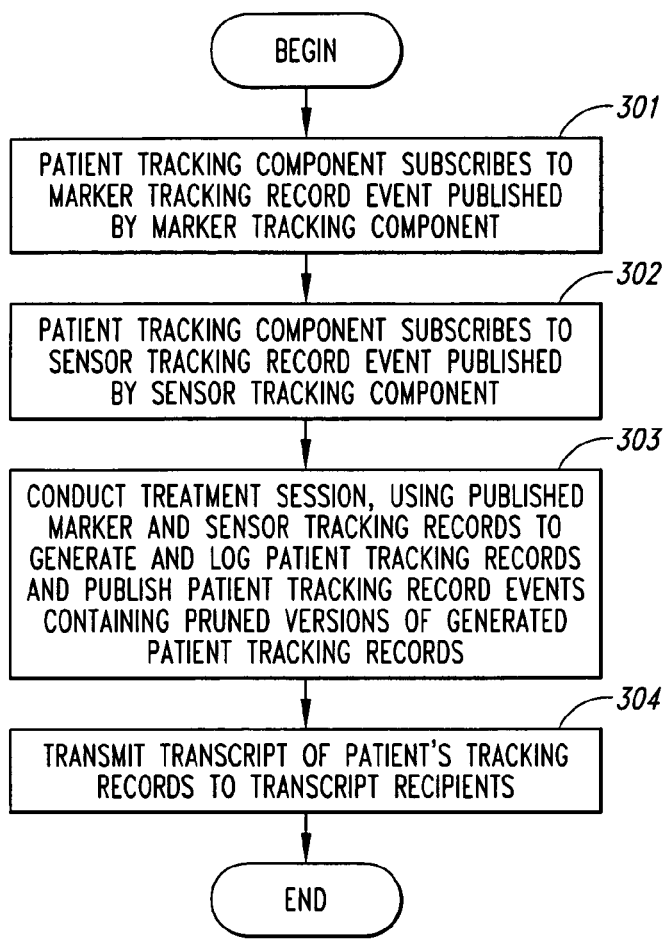
FIG. 3 is a flow diagram showing steps typically performed by the facility in the patient tracking component.

FIG. 3 is a flow diagram showing steps typically performed by the facility in the patient tracking component. In step 301, the patient tracking component subscribes to the marker tracking record object published by the marker tracking component. In step 302, the patient tracking component subscribes to the sensor tracking record object published by the sensor tracking component. In step 303, a treatment session is conducted, during which the patient tracking component uses marker and sensor tracking records contained in published marker and sensor tracking record objects to generate patient tracking records. The patient tracking component logs the generated patient tracking records, and publishes patient tracking record objects containing the generated patient tracking records. In some embodiments, the published patient tracking record objects contain pruned versions of the generated patient tracking records. In step 304, at the conclusion of the patient treatment session, the patient tracking component transmits a transcript of the patient tracking records that were logged to one or more transcript recipients. After step 304, these steps conclude.

Figure 4:
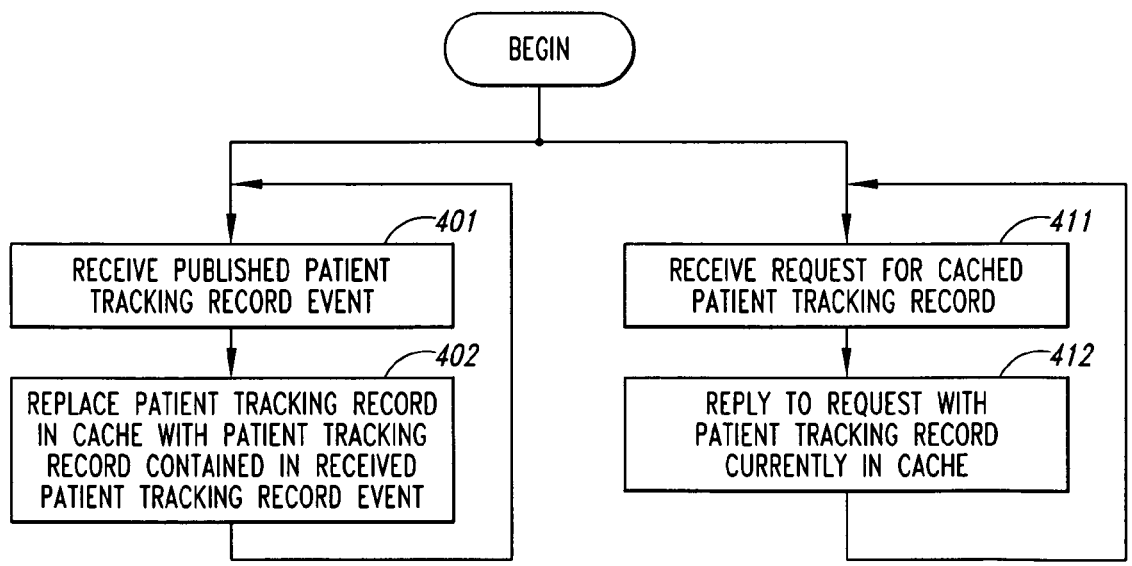
FIG. 4 is a flow diagram showing steps typically performed by the caching component.

FIG. 4 is a flow diagram showing steps typically performed by the caching component. In step 401, the caching component receives a published patient tracking record object from the patient tracking component. In step 402, the caching component replaces the patient tracking record in its cache with the patient tracking record contained in the patient tracking record object received in step 401. After step 402, the caching component continues in step 401 to receive the next published patient tracking record object.

Simultaneously, in step 411, the caching component receives a request for the cached patient tracking record, such as a request submitted by one of the user interface components. In step 412, the caching component replies to the request received in step 411 with the patient tracking record currently contained in the cache. After step 412, the caching component continues in step 411 to receive the next request.

Figure 5:
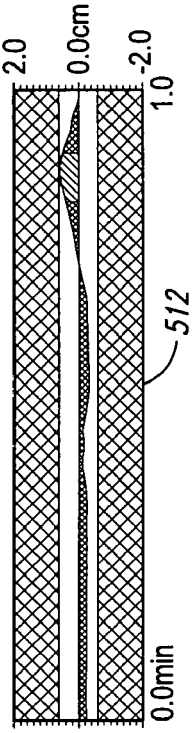
FIG. 5 is a display diagram showing a sample user interface presented by a user interface component.

FIG. 5 is a display diagram showing a sample user interface display presented by a user interface component. The presented display, in addition to other contents, contains numerical and graphical indications of the patient positioning information. In some embodiments, these display contents are updated at a regular periodic rate, such as 10 hertz. In some embodiments, the rate at which these display contents are updated is based upon a time scale configurable by users. FIG. 5 shows this information for the lateral displacement of the patient isocenter from the machine isocenter (i.e., along the x axis) (numerical indication 511 and time-distance graph 512); a longitudinal displacement component (i.e., along the y axis) (numerical indication 521 and time-distance graph 522); and vertical displacement (i.e., along the z axis) (numerical indication 521 and time-distance graph 523). Those skilled in the art will appreciate that a variety of other user interface displays, containing less, more, or different information (including patient tracking information) may be presented by the facility. In addition, the facility may present user interfaces in modes other than visual, such as audible user interfaces.

FIG. 6 is a data structure diagram showing sample contents of the transcript stored by the patient tracking component and/or the database component. The transcript includes a start date and time 601, an end date and time 602, an indication 603 of the number of patient tracking records in the transcript, and an indication 604 of the number of marker tracking records contained in the transcript (not shown). The transcript further includes a table 610 made up of rows, such as row 611-624, each corresponding to a different time. Each row is divided into the following columns: an x displacement column 631 containing the directed distance in the x dimension from the machine isocenter to the patient isocenter, a y displacement column 632, a z displacement column 633, a confidence level column 634 indicating a level of confidence in the record, a result code column 635 indicating a result code, a psi column 636 indicating a first angular component of the orientation of the patient isocenter relative to the machine isocenter, a phi column 637 containing a second angular component of the orientation, a theta column 638 containing a third angular component of the orientation, a measurement date and time column 639 containing an indication of the time at which the measurements were made, and a delta time column 640 indicating the amount of time elapsed between the start date and time and the measurement date and time.

In some embodiments, the data shown in FIG. 6 is stored in forms other than those shown in FIG. 6. For example, Table 1 below shows the data contained in row 617 shown in FIG. 6 expressed in an XML format.

TABLE 1

```
<SessionTargetData>
    <TargetPosition>
        <X>-0.43109733458214217</X>
        <Y>-0.066685713198866473</Y>
        <Z>-0.37997479402471651</Z>
    </TargetPosition>
    <ConfidenceIndex>0</ConfidenceIndex>
    <ResultCode>Okay</ResultCode>
    <Psi>90.000002504478161</Psi>
    <Phi>0</Phi>
    <Theta>0</Theta>
    <MeasurementDateTime>2004-05-25T14:47:45.5468750-07:00
    </MeasurementDateTime>
</SessionTargetData>
```

Those skilled in the art will appreciate that a variety of other formats, including other tag-based markup languages, may be used to store and communicate this information.

In some embodiments, information stored by the facility in the transcript provides a basis for revisiting the treatment session, such as by replaying the user interface display of the session. In some embodiments, the contents of a transcript may be used to perform various forms of retrospective analysis of the session, such as identifying the smallest volume containing every target position throughout the session; determining the percentage of the session during which the target was within a prescribed volume; determining a total dosage of radiation received at the target; etc.

In some embodiments, the facility stores more detailed tracking information than is shown in FIG. 6. For example, in some embodiments, the facility stores, for some or all of the rows, position and/or orientation information for one or more transponders or other markers upon which the facility's determination of target location and/or patient isocenter displacement from treatment isocenter is derived. Where the facility stores this more detailed information, the transcript may be used to re-evaluate the treatment session, such as by using a different approach to derive target location and displacement from lower-level measures.

In some embodiments, the facility passes a transcript or similar data structure to a record and verify system in order to verify that radiation treatment was delivered in accordance with a plan. In some embodiments, the facility itself performs this verification function. For example, in some embodiments, the facility uses the timestamps of the patient location records in the data structure to correlate the patient tracking records with time-indexed information about the status of various radiation treatment parameters, such as those prescribed in the radiation therapy session plan for the session. The facility then uses this time-correlated information to verify that treatment was delivered in accordance with the plan.

Techniques for Sensing Location

A. Overview

FIGS. 7-30 illustrate a system and several components for locating, tracking and monitoring a target within a patient in real time in accordance with embodiments of the present invention. The system and components guide and control the radiation therapy to more effectively treat the target. Several embodiments of the systems described below with reference to FIGS. 7-30 can be used to treat targets in the lung, prostate, head, neck, breast and other parts of the body in accordance with aspects of the present invention. Additionally, the markers and localization systems shown in FIGS. 7-30 may also be used in surgical applications or other medical applications. Like reference numbers refer to like components and features throughout the various figures.

Several embodiments of the invention are directed towards methods for tracking a target, i.e., measuring the position and/or the rotation of a target in substantially real time, in a patient in medical applications. One embodiment of such a method comprises collecting position data of a marker that is substantially fixed relative to the target. This embodiment further includes determining the location of the marker in an external reference frame (i.e., a reference frame outside the patient) and providing an objective output in the external reference frame that is responsive to the location of the marker. The objective output is repeatedly provided at a frequency/periodicity that adequately tracks the location of the target in real time within a clinically acceptable tracking error range. As such, the method for tracking the target enables accurate tracking of the target during diagnostic, planning, treatment or other types of medical procedures. In many specific applications, the objective output is provided within a suitably short latency after collecting the position data and at a sufficiently high frequency to use the data for such medical procedures.

Another specific embodiment is a method for treating a target in a patient with an ionizing radiation beam that includes collecting position information of a marker implanted within a patient at a site relative to the target at a time $t_n$, and providing an objective output indicative of the location of the target based on the position information collected at time $t_n$. The objective output is provided to a memory device, user interface, and/or radiation delivery machine within 2 seconds or less of the time $t_n$ when the position information was collected. This embodiment of the method can further include providing the objective output at a periodicity of 2 seconds or less during at least a portion of a treatment procedure. For example, the method can further include generating a beam of ionizing radiation and directing the beam to a machine isocenter, and continuously repeating the collecting procedure and the providing procedure every 10-200 ms while irradiating the patient with the ionizing radiation beam.

Another embodiment of a method for tracking a target in a patient includes obtaining position information of a marker situated within the patient at a site relative to the target, and determining a location of the marker in an external reference frame based on the position information. This embodiment further includes providing an objective output indicative of the location of the target to a user interface at (a) a sufficiently high frequency so that pauses in representations of the target location at the user interface are not readily discernable by a human, and (b) a sufficiently low latency to be at least substantially contemporaneous with obtaining the position information of the marker.

Another embodiment of the invention is directed toward a method of treating a target of a patient with an ionizing radiation beam by generating a beam of ionizing radiation and directing the beam relative to the target. This method further includes collecting position information of a marker implanted within the patient at a site relative to the target while directing the beam toward the beam isocenter. Additionally, this method includes providing an objective output indicative of a location of the target relative to the beam isocenter based on the collected position information. This method can further include correlating the objective output with a parameter of the beam, and controlling the beam based upon the objective output. For example, the beam can be gated to only irradiate the patient when the target is within a desired irradiation zone. Additionally, the patient can be moved automatically and/or the beam can be shaped automatically according to the objective output to provide dynamic control in real time that maintains the target at a desired position relative to the beam isocenter while irradiating the patient.

Various embodiments of the invention are described in this section to provide specific details for a thorough understanding and enabling description of these embodiments. A person skilled in the art, however, will understand that the invention may be practiced without several of these details, or that additional details can be added to the invention. Where the context permits, singular or plural terms may also include the plural or singular term, respectively. Moreover, unless the word "or" is expressly limited to mean only a single item exclusive from the other items in reference to a list of at least two items, then the use of "or" in such a list is to be interpreted as including (a) any single item in the list, (b) all of the items in the list, or (c) any combination of items in the list. Additionally, the term "comprising" is used throughout to mean including at least the recited feature(s) such that any greater number of the same feature and/or types of other features or components are not precluded.

B. Radiation Therapy Systems with Real Time Tracking Systems

Figure 7:
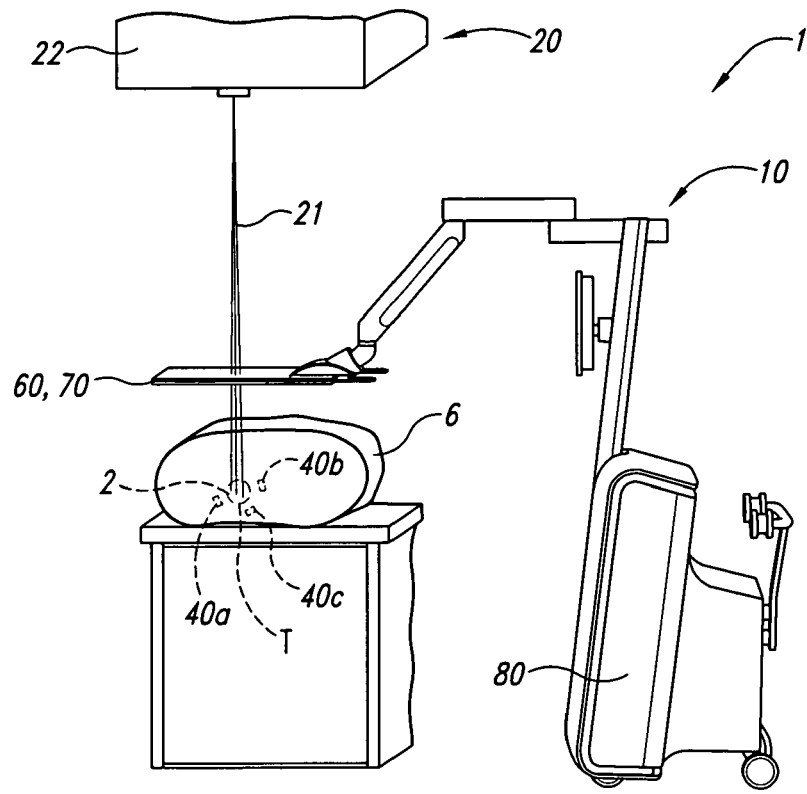
FIG. 7 is a side elevation view of a tracking system for use in localizing and monitoring a target in accordance with an embodiment of the present invention. Excitable markers are shown implanted in or adjacent to a target in the patient.
Figure 8:
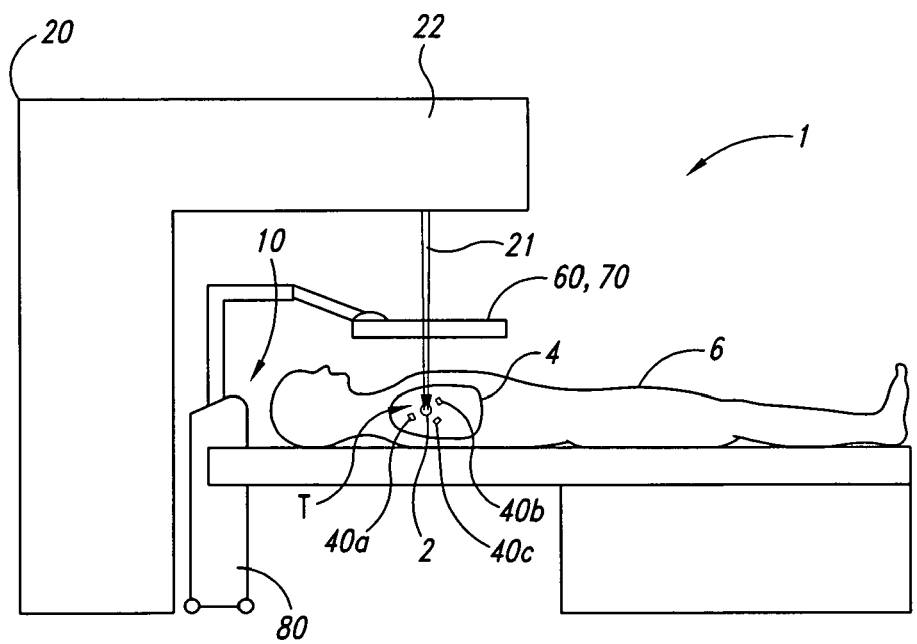
FIG. 8 is a schematic elevation view of the patient on a movable support table and of markers implanted in the patient.

FIGS. 7 and 8 illustrate various aspects of a radiation therapy system 1 for applying guided radiation therapy to a target 2 (e.g., a tumor) within a lung 4, prostate, breast, head, neck or other part of a patient 6. The radiation therapy system 1 has a localization system 10 and a radiation delivery device 20. The localization system 10 is a tracking unit that locates and tracks the actual position of the target 2 in real time during treatment planning, patient setup, and/or while applying ionizing radiation to the target from the radiation delivery device. Thus, although the target 2 may move within the patient because of breathing, organ filling/emptying, cardiac functions or other internal movement as described above, the localization system 10 accurately tracks the motion of the target relative to the external reference frame of the radiation delivery device or other external reference frame outside of the patient to accurately deliver radiation within a small margin around the target. The localization system 10 can also monitor the configuration and trajectory of the marker to provide an early indicator of a change in the tumor without using ionizing radiation. Moreover, the localization system 10 continuously tracks the target and provides objective data (e.g., three-dimensional coordinates in an absolute reference frame) to a memory device, user interface, linear accelerator, and/or other device. The system 1 is described below in the context of guided radiation therapy for treating a tumor or other target in the lung of the patient, but the system can be used for tracking and monitoring the prostate gland or other targets within the patient for other therapeutic and/or diagnostic purposes.

The radiation delivery source of the illustrated embodiment is an ionizing radiation device 20 (i.e., a linear accelerator). Suitable linear accelerators are manufactured by Varian Medical Systems, Inc. of Palo Alto, Calif.; Siemens Medical Systems, Inc. of Iselin, N.J.; Elekta Instruments, Inc. of Iselin, N.J.; or Mitsubishi Denki Kabushik Kaisha of Japan. Such linear accelerators can deliver conventional single or multi-field radiation therapy, 3D conformal radiation therapy (3D CRT), intensity modulated radiation therapy (IMRT), stereotactic radiotherapy, and tomo therapy. The radiation delivery source 20 can deliver a gated, contoured or shaped beam 21 of ionizing radiation from a movable gantry 22 to an area or volume at a known location in an external, absolute reference frame relative to the radiation delivery source 20. The point or volume to which the ionizing radiation beam 21 is directed is referred to as the machine isocenter.

The tracking system includes the localization system 10 and one or more markers 40. The localization system 10 determines the actual location of the markers 40 in a three-dimensional reference frame, and the markers 40 are typically implanted within the patient 6. In the embodiment illustrated in FIGS. 7 and 8, more specifically, three markers identified individually as markers 40a-c are implanted in or near the lung 4 of the patient 6 at locations in or near the target 2. In other applications, a single marker, two markers, or more than three markers can be used depending upon the particular application. Two markers, for example, are desirable because the location of the target can be determined accurately, and also because any relative displacement between the two markers over time can be used to monitor marker migration in the patient. The markers 40 are desirably placed relative to the target 2 such that the markers 40 are at least substantially fixed relative to the target 2 (e.g., the markers move directly with the target or at least in direct proportion to the movement of the target). The relative positions between the markers 40 and the relative positions between a target isocenter T of the target 2 and the markers 40 can be determined with respect to an external reference frame defined by a CT scanner or other type of imaging system during a treatment planning stage before the patient is placed on the table. In the particular embodiment of the system 1 illustrated in FIGS. 7 and 8, the localization system 10 tracks the three-dimensional coordinates of the markers 40 in real time relative to an absolute external reference frame during the patient setup process and while irradiating the patient to mitigate collateral effects on adjacent healthy tissue and to ensure that the desired dosage is applied to the target.

C. General Aspects of Markers and Localization Systems

Figure 9:
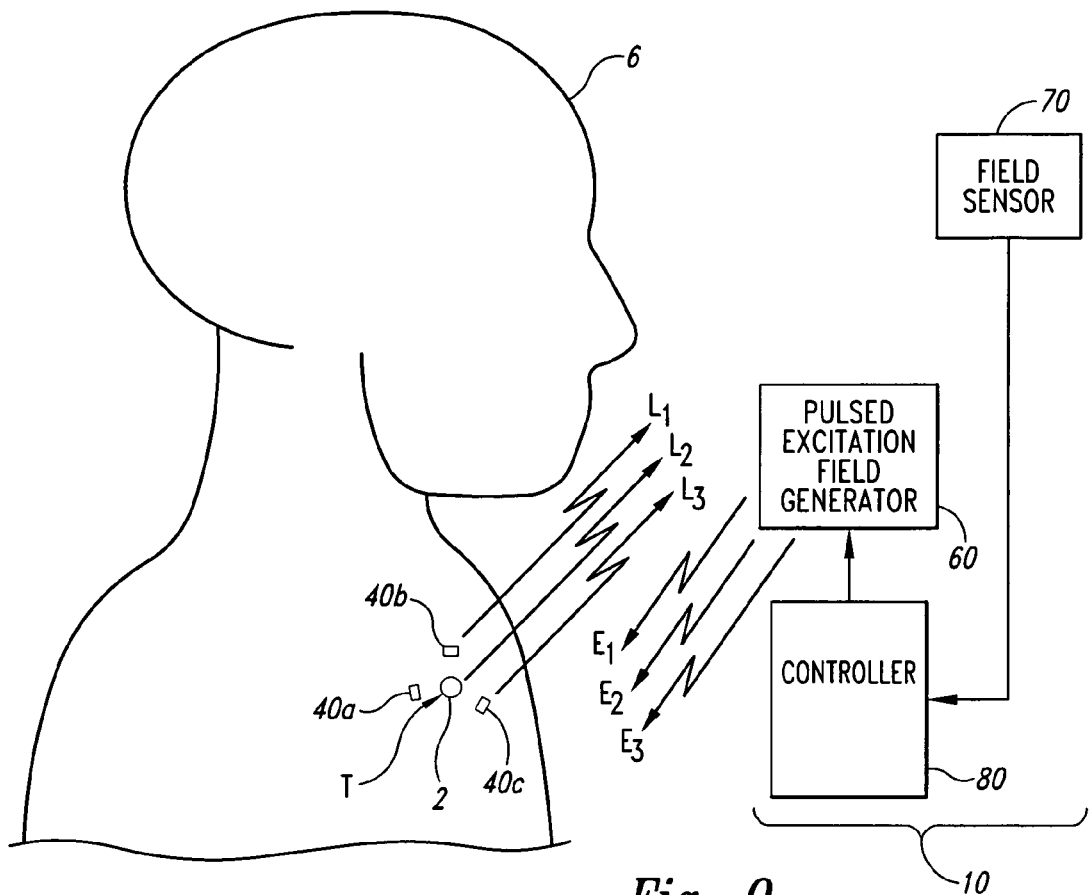
FIG. 9 is a side view schematically illustrating a localization system and a plurality of markers implanted in a patient in accordance with an embodiment of the invention.

FIG. 9 is a schematic view illustrating the operation of an embodiment of the localization system 10 and markers 40*a-c* for treating a tumor or other target in the patient. The localization system 10 and the markers 40*a-c* are used to determine the location of the target 2 (FIGS. 7 and 8) before, during and after radiation sessions. More specifically, the localization system 10 determines the locations of the markers 40*a-c* and provides objective target position data to a memory, user interface, linear accelerator and/or other device in real time during setup, treatment, deployment, simulation, surgery, and/or other medical procedures. In one embodiment of the localization system, real time means that indicia of objective coordinates are provided to a user interface at (a) a sufficiently high refresh rate (i.e., frequency) such that pauses in the data are not humanly discernable and (b) a sufficiently low latency to be at least substantially contemporaneous with the measurement of the location signal. In other embodiments, real time is defined by higher frequency ranges and lower latency ranges for providing the objective data to a radiation delivery device. In some embodiments, real time is defined as providing objective data periodically responsive to the location of the markers, with a sufficiently short period that tracking errors are within clinically acceptable limits.

1. Localization Systems

The localization system 10 includes an excitation source 60 (e.g., a pulsed magnetic field generator), a sensor assembly 70, and a controller 80 coupled to both the excitation source 60 and the sensor assembly 70. The excitation source 60 generates an excitation energy to energize at least one of the markers 40*a-c* in the patient 6 (FIG. 7). The embodiment of the excitation source 60 shown in FIG. 9 produces a pulsed magnetic field at different frequencies. For example, the excitation source 60 can frequency multiplex the magnetic field at a first frequency $E_1$ to energize the first marker 40*a*, a second frequency $E_2$ to energize the second marker 40*b*, and a third frequency $E_3$ to energize the third marker 40*c*. In response to the excitation energy, the markers 40*a-c* generate location signals $L_{1-3}$ at unique response frequencies. More specifically, the first marker 40*a* generates a first location signal $L_1$ at a first frequency in response to the excitation energy at the first frequency $E_1$, the second marker 40*b* generates a second location signal $L_2$ at a second frequency in response to the excitation energy at the second frequency $E_2$, and the third marker 40*c* generates a third location signal $L_3$ at a third frequency in response to the excitation energy at the third frequency $E_3$. In an alternative embodiment with two markers, the excitation source generates the magnetic field at frequencies $E_1$ and $E_2$, and the markets 40*a-b* generate location signals $L_1$ and $L_2$, respectively.

The sensor assembly 70 can include a plurality of coils to sense the location signals $L_{1-3}$ from the markers 40*a-c*. The sensor assembly 70 can be a flat panel having a plurality of coils that are at least substantially coplanar relative to each other. In other embodiments, the sensor assembly 70 may be a non-planar array of coils.

The controller 80 includes hardware, software or other computer-operable media containing instructions that operate the excitation source 60 to multiplex the excitation energy at the different frequencies $E_{1-3}$. For example, the controller 80 causes the excitation source 60 to generate the excitation energy at the first frequency $E_1$ for a first excitation period, and then the controller 80 causes the excitation source 60 to terminate the excitation energy at the first frequency $E_1$ for a first sensing phase during which the sensor assembly 70 senses the first location signal $L_1$ from the first marker 40*a* without the presence of the excitation energy at the first frequency $E_1$. The controller 80 then causes the excitation source 60 to: (a) generate the second excitation energy at the second frequency $E_2$ for a second excitation period; and (b) terminate the excitation energy at the second frequency $E_2$ for a second sensing phase during which the sensor assembly 70 senses the second location signal $L_2$ from the second marker 40*b* without the presence of the second excitation energy at the second frequency $E_2$. The controller 80 then repeats this operation with the third excitation energy at the third frequency $E_3$ such that the third marker 40*c* transmits the third location signal $L_3$ to the sensor assembly 70 during a third sensing phase. As such, the excitation source 60 wirelessly transmits the excitation energy in the form of pulsed magnetic fields at the resonant frequencies of the markers 40*a-c* during excitation periods, and the markers 40*a-c* wirelessly transmit the location signals $L_{1-3}$ to the sensor assembly 70 during sensing phases. It will be appreciated that the excitation and sensing phases can be repeated to permit averaging of the sensed signals to reduce noise.

The computer-operable media in the controller 80, or in a separate signal processor, or other computer also includes instructions to determine the absolute positions of each of the markers 40*a-c* in a three-dimensional reference frame. Based on signals provided by the sensor assembly 70 that correspond to the magnitude of each of the location signals $L_{1-3}$, the controller 80 and/or a separate signal processor calculates the absolute coordinates of each of the markers 40*a-c* in the three-dimensional reference frame. The absolute coordinates of the markers 40*a-c* are objective data that can be used to calculate the coordinates of the target in the reference frame. When multiple markers are used, the rotation of the target can also be calculated.

2. Real Time Tracking

The localization system 10 and at least one of a marker 40 enables real time tracking of the target 2 relative to the machine isocenter or another external reference frame outside of the patient during treatment planning, set up, radiation sessions, and at other times of the radiation therapy process. In many embodiments, real time tracking means collecting position data of the markers, determining the locations of the markers in an external reference frame, and providing an objective output in the external reference frame that is responsive to the location of the markers. The objective output is provided at a frequency that adequately tracks the target in real time and/or a latency that is at least substantially contemporaneous with collecting the position data (e.g., within a generally concurrent period of time).

For example, several embodiments of real time tracking are defined as determining the locations of the markers and calculating the location of the target relative to the machine isocenter at (a) a sufficiently high frequency so that pauses in representations of the target location at a user interface do not interrupt the procedure or are readily discernable by a human, and (b) a sufficiently low latency to be at least substantially contemporaneous with the measurement of the location signals from the markers. Alternatively, real time means that the location system 10 calculates the absolute position of each individual marker 40 and/or the location of the target at a periodicity of 1 ms to 5 seconds, or in many applications at a periodicity of approximately 10-100 ms, or in some specific applications at a periodicity of approximately 20-50 ms. In applications for user interfaces, for example, the periodicity can be 12.5 ms (i.e., a frequency of 80 Hz), 16.667 ms (60 Hz), 20 ms (50 Hz), and/or 50 ms (20 Hz).

Alternatively, real time tracking can further mean that the location system 10 provides the absolute locations of the markers 40 and/or the target 2 to a memory device, user interface, linear accelerator or other device within a latency of 10 ms to 5 seconds from the time the localization signals were transmitted from the markers 40. In more specific applications, the location system generally provides the locations of the markers 40 and/or target 2 within a latency of about 20-50 ms. The location system 10 accordingly provides real time tracking to monitor the position of the markers 40 and/or the target 2 with respect to an external reference frame in a manner that is expected to enhance the efficacy of radiation therapy because higher radiation doses can be applied to the target and collateral effects to healthy tissue can be mitigated.

Alternatively, real-time tracking can further be defined by the tracking error. Measurements of the position of a moving target are subject to motion-induced error, generally referred to as a tracking error. According to aspects of the present invention, the localization system 10 and at least one marker 4 enable real time tracking of the target 2 relative to the machine isocenter or another external reference frame with a tracking error that is within clinically meaningful limits.

Tracking errors are due to two limitations exhibited by any practical measurement system, specifically (a) latency between the time the target position is sensed and the time the position measurement is made available, and (b) sampling delay due to the periodicity of measurements. For example, if a target is moving at 5 cm/s and a measurement system has a latency of 200 ms, then position measurements will be in error by 1 cm. The error in this example is due to latency alone, independent of any other measurement errors, and is simply due to the fact that the target has moved between the time its position is sensed and the time the position measurement is made available for use. If this exemplary measurement system further has a sampling periodicity of 200 ms (i.e., a sampling frequency of 5 Hz), then the peak tracking error increases to 2 cm, with an average tracking error of 1.5 cm.

For a real time tracking system to be useful in medical applications, it is desirable to keep the tracking error within clinically meaningful limits. For example, in a system for tracking motion of a tumor in a lung for radiation therapy, it may be desirable to keep the tracking error within 5 mm. Acceptable tracking errors may be smaller when tracking other organs for radiation therapy. In accordance with aspects of the present invention, real time tracking refers to measurement of target position and/or rotation with tracking errors that are within clinically meaningful limits.

In some embodiments, the system temporally filters the measurements of the marker locations, or the calculated location of the target, in order to reduce the effects of additive noise or other measurement errors. Such filtering has the effect of increasing the latency, hence the tracking error, of the system. Conversely, reducing the filtering has the effect of reducing the tracking error, at the price of increasing the effects of noise. In some embodiments, the system periodically measures the vector velocity (or a similar state variable) of the markers or the target, in addition to their locations. Such an approach can improve the accuracy of subsequent location measurements. In this case, filtering can be applied to measurements of vector velocity as well. Techniques to implement temporal filtering are well known to those skilled in the art, and include recursive and non-recursive digital filters, and Kalman and other non-linear filters. References herein to location data, or digital location indications, or the like, include those data which have been filtered, or derived from filtered measurements.

The system described herein uses one or more markers to serve as registration points to characterize target location, rotation, and motion. In accordance with aspects of the invention, the markers have a substantially fixed relationship with the target. If the markers did not have a substantially fixed relationship with the target another type of tracking error would be incurred. This generally requires the markers to be fixed or implanted sufficiently close to the target in order that tracking errors be within clinically meaningful limits, thus, the markers may be placed in tissue or bone that exhibits representative motion of the target. For example, with respect to the prostate, tissue that is representative of the target's motion would include tissue in close proximity or adjacent to the prostate. Tissue adjacent to a target involving the prostate may include the prostate gland, the tumor itself, or tissue within a specified radial distance from the target. With respect to the prostate, tracking tissue that is a 5 cm radial distance from the target would provide representative motion that is clinically useful to the motion of the target. In accordance with alternative target tracking locations, the radial distance may be greater or lesser.

According to aspects of the present invention, the marker motion is a surrogate for the motion of the target. Accordingly, the marker is placed such that it moves in direct correlation to the target being tracked. Depending on the target being tracked, the direct correlation relationship between the target and the marker will vary. For example, in long bones, the marker may be place anywhere along the bone to provide motion that directly correlate to target motion in the bone. With respect to soft tissue that moves substantially in response to the bony anatomy, for example, the head and neck, the marker may be placed in a bite block to provide surrogate motion in direct correlation with target motion. With respect to soft tissue and as discussed in detail above, the target may be placed in adjacent soft tissue to provide a surrogate having direct correlation to target motion.

Figure 10:
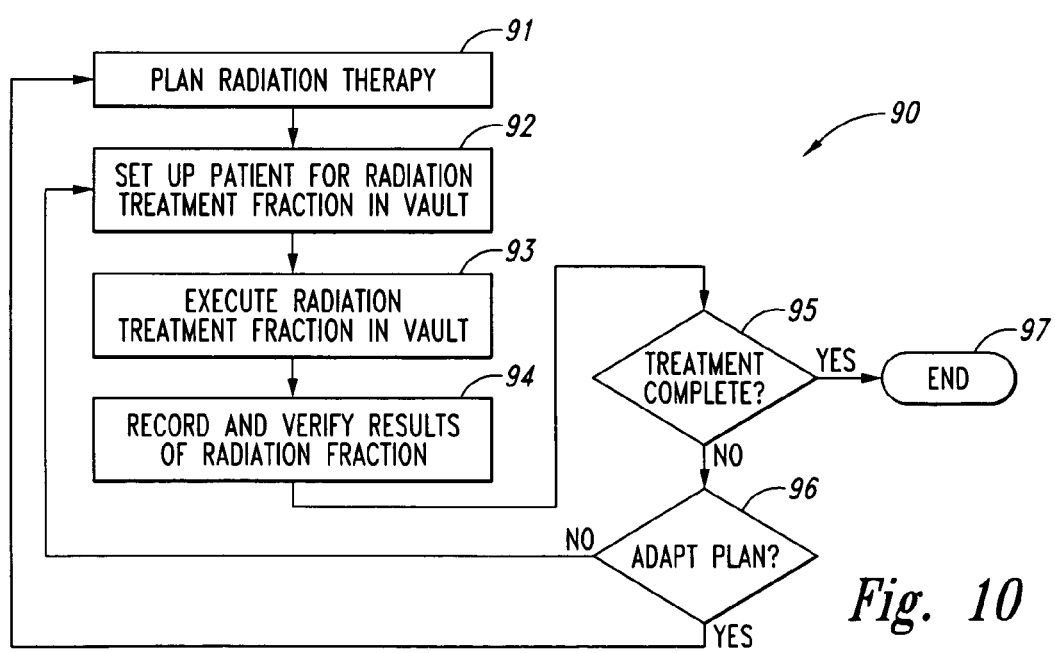
FIG. 10 is a flow diagram of an integrated radiation therapy process that uses real time target tracking for radiation therapy in accordance with an embodiment of the invention.
Figure 11A:
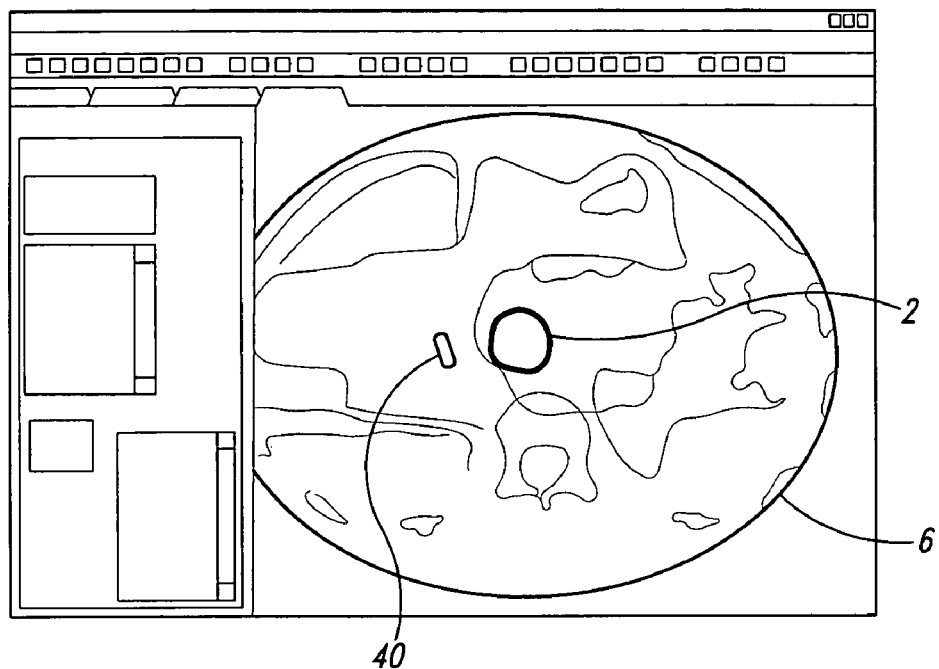
FIG. 11A is a representation of a CT image illustrating an aspect of a system and method for real time tracking of targets in radiation therapy and other medical applications.
Figure 11B:
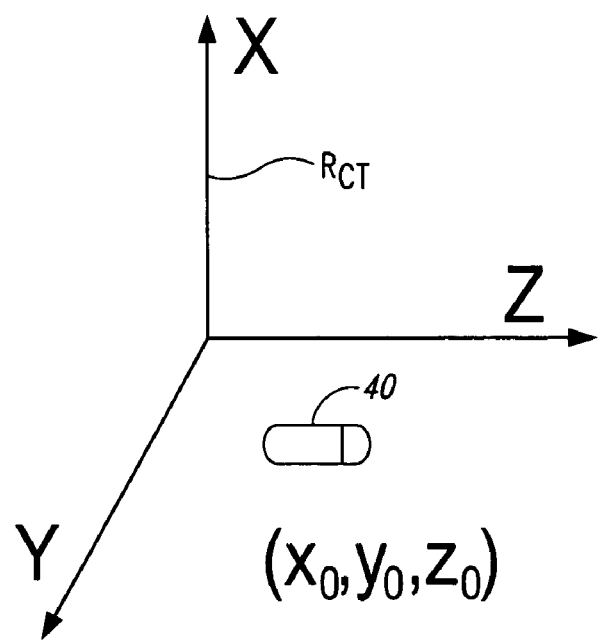
FIG. 11B is a diagram schematically illustrating a reference frame of a CT scanner.

FIG. 10 is a flow diagram illustrating several aspects and uses of real time tracking to monitor the location and the status of the target. In this embodiment, an integrated method 90 for radiation therapy includes a radiation planning procedure 91 that determines the plan for applying the radiation to the patient over a number of radiation fractions. The radiation planning procedure 91 typically includes an imaging stage in which images of a tumor or other types of targets are obtained using X-rays, CT, MRI, or ultrasound imaging. The images are analyzed by a person to measure the relative distances between the markers and the relative position between the target and the markers. FIG. 11A, for example, is a representation of a CT image showing a cross-section of the patient 6, the target 2, and a marker 40. Referring to FIG. 11B, the coordinates $(x_0, y_0, z_0)$ of the marker 40 in a reference frame $R_{CT}$ of the CT scanner can be determined by an operator. The coordinates of the tumor can be determined in a similar manner to ascertain the offset between the marker and the target.

The radiation planning procedure 91 can also include tracking the targets using the localization system 10 (FIG. 9) in an observation area separate from the imaging equipment. The markers 40 (FIG. 9) can be tracked to identify changes in the configuration (e.g., size/shape) of the target over time and to determine the trajectory of the target caused by movement of the target within the patient (e.g., simulation). For many treatment plans, the computer does not need to provide objective output data of the marker or target locations to a user in real time, but rather the data can be recorded in real time. Based on the images obtained during the imaging stage and the additional data obtained by tracking the markers using the localization system 10 in a simulation procedure, a treatment plan is developed for applying the radiation to the target.

Figure 12:
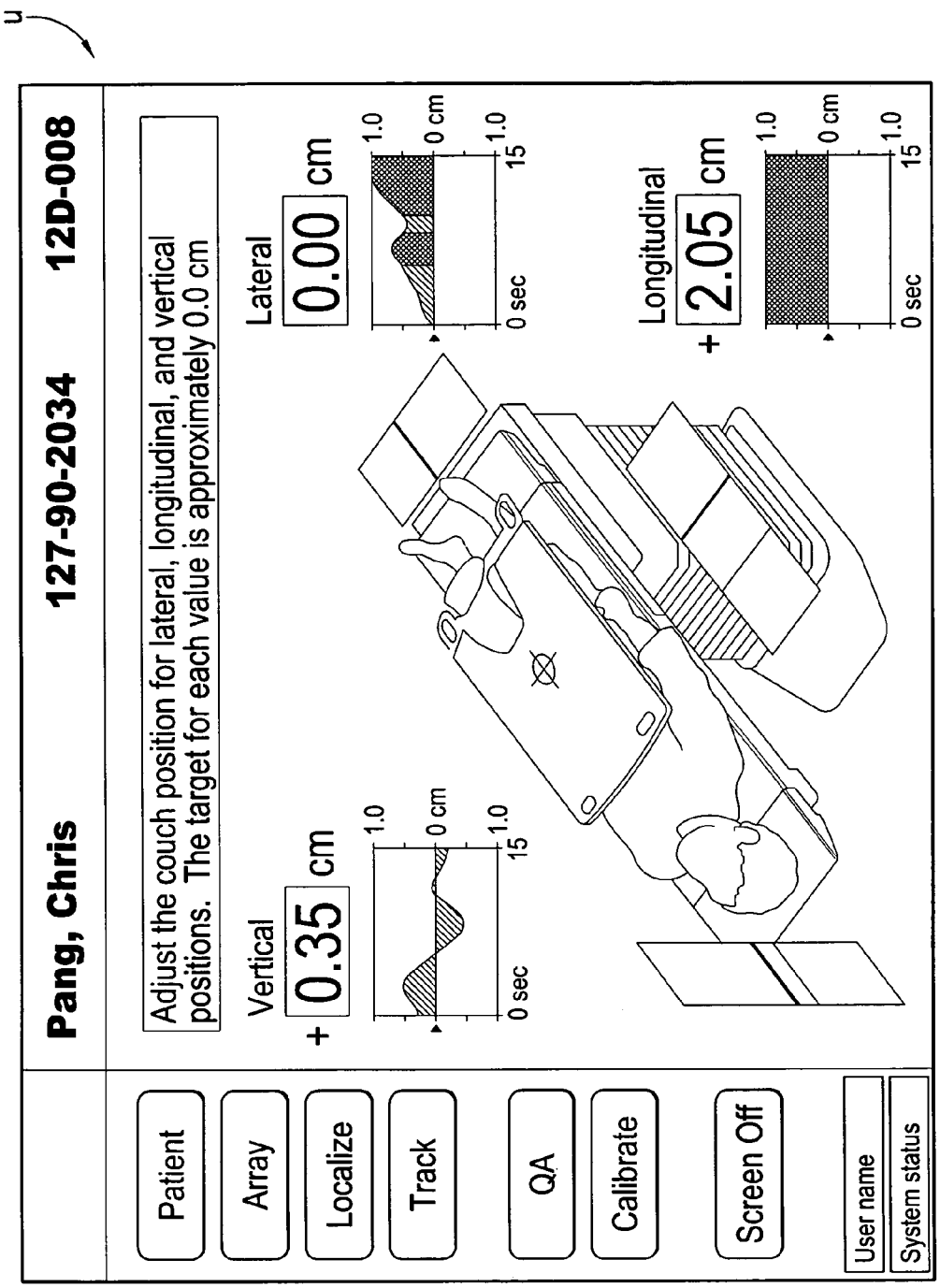
FIG. 12 is a screenshot of a user interface for displaying an objective output in accordance with an embodiment of the invention.

The localization system 10 and the markers 40 enable an automated patient setup process for delivering the radiation. After developing a treatment plan, the method 90 includes a setup procedure 92 in which the patient is positioned on a movable support table so that the target and markers are generally adjacent to the sensor assembly. As described above, the excitation source is activated to energize the markers, and the sensors measure the strength of the signals from the markers. The computer controller then (a) calculates objective values of the locations of the markers and the target relative to the machine isocenter, and (b) determines an objective offset value between the position of the target and the machine isocenter. Referring to FIG. 12, for example, the objective offset values can be provided to a user interface that displays the vertical, lateral and longitudinal offsets of the target relative to the machine isocenter. A user interface may, additionally or instead, display target rotation.

One aspect of several embodiments of the localization system 10 is that the objective values are provided to the user interface or other device by processing the position data from the field sensor 70 in the controller 80 or other computer without human interpretation of the data received by the field sensor 70. If the offset value is outside of an acceptable range, the computer automatically activates the control system of the support table to move the tabletop relative to the machine isocenter until the target isocenter is coincident with the machine isocenter. The computer controller generally provides the objective output data of the offset to the table control system in real time as defined above. For example, because the output is provided to the radiation delivery device, it can be at a high rate (1-20 ms) and a low latency (10-20 ms). If the output data is provided to a user interface in addition to or in lieu of the table controller, it can be at a relatively lower rate (20-50 ms) and higher latency (50-200 ms).

In one embodiment, the computer controller also determines the position and orientation of the markers relative to the position and orientation of simulated markers. The locations of the simulated markers are selected so that the target will be at the machine isocenter when the real markers are at the selected locations for the simulated markers. If the markers are not properly aligned and oriented with the simulated markers, the support table is adjusted as needed for proper marker alignment. This marker alignment properly positions the target along six dimensions, namely X, Y, Z, pitch, yaw, and roll. Accordingly, the patient is automatically positioned in the correct position and rotation relative to the machine isocenter for precise delivery of radiation therapy to the target.

Figure 13:
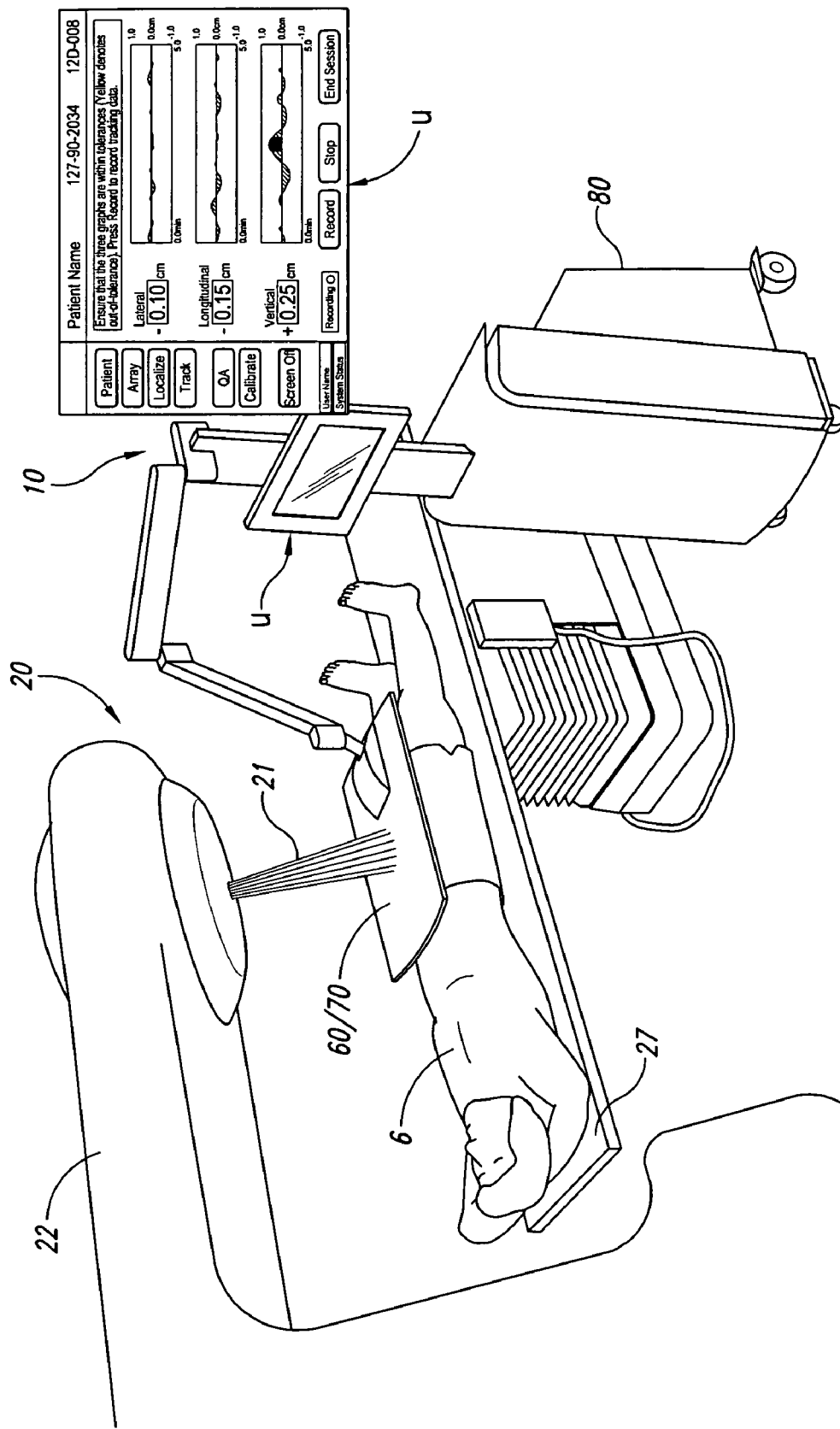
FIG. 13 is an isometric view of a radiation session in accordance with an embodiment of the invention.

Referring back to FIG. 10, the method 90 further includes a radiation session 93. FIG. 13 shows a further aspect of an automated process in which the localization system 10 tracks the target during the radiation session 93 and controls the radiation delivery device 20 according to the offset between target and the machine isocenter. For example, if the position of the target is outside of a permitted degree or range of displacement from the machine isocenter, the localization system 10 sends a signal to interrupt the delivery of the radiation or prevent initial activation of the beam. In another embodiment, the localization system 10 sends signals to automatically reposition a tabletop 27 and the patient 6 (as a unit) so that the target isocenter remains within a desired range of the machine isocenter during the radiation session 93 even if the target moves. In still another embodiment, the localization system 10 sends signals to activate the radiation only when the target is within a desired range of the machine isocenter (e.g., gated therapy). In the case of treating a target in the lung, one embodiment of gated therapy includes tracking the target during inspiration/expiration, having the patient hold his/her breath at the end of an inspiration/expiration cycle, and activating the beam 21 when the computer 80 determines that the objective offset value between the target and the machine isocenter is within a desired range. Accordingly, the localization system enables dynamic adjustment of the table 27 and/or the beam 21 in real time while irradiating the patient. This is expected to ensure that the radiation is accurately delivered to the target without requiring a large margin around the target.

The localization system provides the objective data of the offset and/or rotation to the linear accelerator and/or the patient support table in real time as defined above. For example, as explained above with respect to automatically positioning the patent support table during the setup procedure 92, the localization system generally provides the objective output to the radiation delivery device at least substantially contemporaneously with obtaining the position data of the markers and/or at a sufficient frequency to track the target in real time. The objective output, for example, can be provided at a short periodicity (1-20 ms) and a low latency (10-20 ms) such that signals for, controlling the beam 21 can be sent to the radiation delivery device 20 in the same time periods during a radiation session. In another example of real time tracking, the objective output is provided a plurality of times during an "on-beam" period (e.g., 2, 5, 10 or more times while the beam is on). In the case of terminating or activating the radiation beam, or adjusting the leafs of a beam collimator, it is generally desirable to maximize the refresh rate and minimize the latency. In some embodiments, therefore, the localization system may provide the objective output data of the target location and/or the marker locations at a periodicity of 10 ms or less and a latency of 10 ms or less.

The method 90 further includes a verification procedure 94 in which the real time objective output data from the radiation session 93 is compared to the status of the parameters of the radiation beam. For example, the target locations can be correlated with the beam intensity, beam position, and collimator configuration at corresponding time intervals during the radiation session 93. This correlation can be used to determine the dose of radiation delivered to discrete regions in and around the target. This information can also be used to determine the effects of radiation on certain areas of the target by noting changes in the target configuration or the target trajectory.

The method 90 can further include a first decision (Block 95) in which the data from the verification procedure 94 is analyzed to determine whether the treatment is complete. If the treatment is not complete, the method 90 further includes a second decision (Block 96) in which the results of the verification procedure are analyzed to determine whether the treatment plan should be revised to compensate for changes in the target. If revisions are necessary, the method can proceed with repeating the planning procedure 91. On the other hand, if the treatment plan is providing adequate results, the method 90 can proceed by repeating the setup procedure 92, radiation session 93, and verification procedure 94 in a subsequent fraction of the radiation therapy.

The localization system 10 provides several features, either individually or in combination with each other, that enhance the ability to accurately deliver high doses of radiation to targets within tight margins. For example, many embodiments of the localization system use leadless markers that are implanted in the patient so that they are substantially fixed with respect to the target. The markers accordingly move either directly with the target or in a relationship proportional to the movement of the target. As a result, internal movement of the target caused by respiration, organ filling, cardiac functions, or other factors can be identified and accurately tracked before, during and after medical procedures. Moreover, many aspects of the localization system 10 use a non-ionizing energy to track the leadless markers in an external, absolute reference frame in a manner that provides objective output. In general, the objective output is determined in a computer system without having a human interpret data (e.g., images) while the localization system 10 tracks the target and provides the objective output. This significantly reduces the latency between the time when the position of the marker is sensed and the objective output is provided to a device or a user. For example, this enables an objective output responsive to the location of the target to be provided at least substantially contemporaneously with collecting the position data of the marker. The system also effectively eliminates inter-user variability associated with subjective interpretation of data (e.g., images).

D. Specific Embodiments of Markers and Localization Systems

The following specific embodiments of markers, excitation sources, sensors and controllers provide additional details to implement the systems and processes described above with reference to FIGS. 7-13. The present inventors overcame many challenges to develop markers and localization systems that accurately determine the location of a marker which (a) produces a wirelessly transmitted location signal in response to a wirelessly transmitted excitation energy, and (b) has a cross-section small enough to be implanted in the lung, prostate, or other part of a patient. Systems with these characteristics have several practical advantages, including (a) not requiring ionization radiation, (b) not requiring line-of-sight between the markers and sensors, and (c) effecting an objective measurement of a target's location and/or rotation. The following specific embodiments are described in sufficient detail to enable a person skilled in the art to make and use such a localization system for radiation therapy involving a tumor in the patient, but the invention is not limited to the following embodiments of markers, excitation sources, sensor assemblies and/or controllers.

1. Markers

Figure 14A:
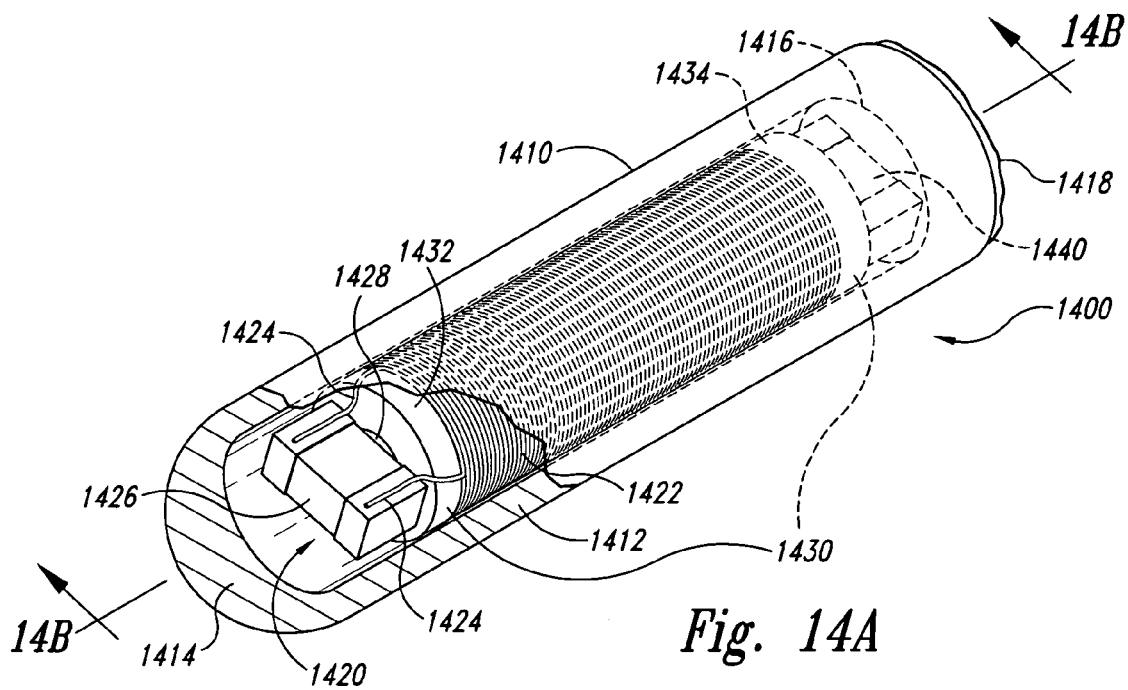
FIG. 14A is an isometric view of a marker for use with a localization system in accordance with an embodiment of the invention.

FIG. 14A is an isometric view of a marker 1400 for use with the localization system 10 (FIGS. 7-13). The embodiment of the marker 1400 shown in FIG. 14A includes a casing 1410 and a magnetic transponder 1420 (e.g., a resonating circuit) in the casing 1410. The casing 1410 is a barrier configured to be implanted in the patient, or encased within the body of an instrument. The casing 1410 can alternatively be configured to be adhered externally to the skin of the patient. The casing 1410 can be a generally cylindrical capsule that is sized to fit within the bore of a small introducer, such as bronchoscope or percutaneous trans-thoracic implanter, but the casing 1410 can have other configurations and be larger or smaller. The casing 1410, for example, can have barbs or other features to anchor the casing 1410 in soft tissue or an adhesive for attaching the casing 1410 externally to the skin of a patient. Suitable anchoring mechanisms for securing the marker 1400 to a patient are disclosed in International Publication No. WO 02/39917 A1, which designates the United States and is incorporated herein by reference. In one embodiment, the casing 1410 includes (a) a capsule or shell 1412 having a closed end 1414 and an open end 1416, and (b) a sealant 1418 in the open end 1416 of the shell 1412. The casing 1410 and the sealant 1418 can be made from plastics, ceramics, glass or other suitable biocompatible materials.

The magnetic transponder 1420 can include a resonating circuit that wirelessly transmits a location signal in response to a wirelessly transmitted excitation field as described above. In this embodiment, the magnetic transponder 1420 comprises a coil 1422 defined by a plurality of windings of a conductor 1424. Many embodiments of the magnetic transponder 1420 also include a capacitor 1426 coupled to the coil 1422. The coil 1422 resonates at a selected resonant frequency. The coil 1422 can resonate at a resonant frequency solely using the parasitic capacitance of the windings without having a capacitor, or the resonant frequency can be produced using the combination of the coil 1422 and the capacitor 1426. The coil 1422 accordingly generates an alternating magnetic field at the selected resonant frequency in response to the excitation energy either by itself or in combination with the capacitor 1426. The conductor 1424 of the illustrated embodiment can be hot air or alcohol bonded wire having a gauge of approximately 45-52. The coil 1422 can have 800-1000 turns, and the windings are preferably wound in a tightly layered coil. The magnetic transponder 1420 can further include a core 1428 composed of a material having a suitable magnetic permeability. For example, the core 1428 can be a ferromagnetic element composed of ferrite or another material. The magnetic transponder 1420 can be secured to the casing 1410 by an adhesive 1429.

The marker 1400 also includes an imaging element that enhances the radiographic image of the marker to make the marker more discernible in radiographic images. The imaging element also has a radiographic profile in a radiographic image such that the marker has a radiographic centroid at least approximately coincident with the magnetic centroid of the magnetic transponder 1420. As explained in more detail below, the radiographic and magnetic centroids do not need to be exactly coincident with each other, but rather can be within an acceptable range.

Figure 14B:
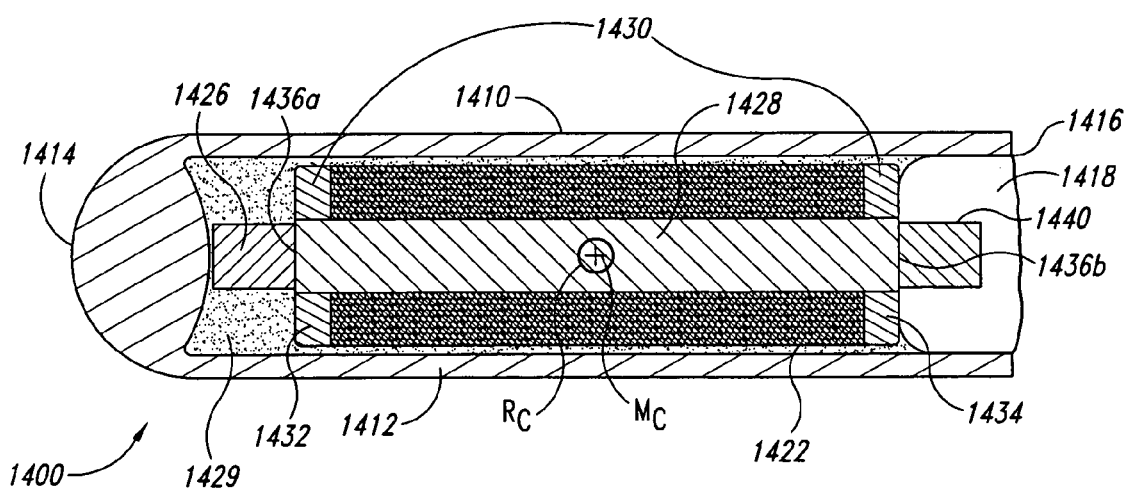
FIG. 14B is a cross-sectional view of the marker of FIG. 14A taken along line 14B-14B.

FIG. 14B is a cross-sectional view of the marker 1400 along line 14B-14B of FIG. 14A that illustrates an imaging element 1430 in accordance with an embodiment of the invention. The imaging element 1430 illustrated in FIGS. 14A-B includes a first contrast element 1432 and second contrast element 1434. The first and second contrast elements 1432 and 1434 are generally configured with respect to the magnetic transponder 1420 so that the marker 1400 has a radiographic centroid $R_c$ that is at least substantially coincident with the magnetic centroid $M_c$ of the magnetic transponder 1420. For example, when the imaging element 1430 includes two contrast elements, the contrast elements can be arranged symmetrically with respect to the magnetic transponder 1420 and/or each other. The contrast elements can also be radiographically distinct from the magnetic transponder 1420. In such an embodiment, the symmetrical arrangement of distinct contrast elements enhances the ability to accurately determine the radiographic centroid of the marker 1400 in a radiographic image.

The first and second contrast elements 1432 and 1434 illustrated in FIGS. 14A-B are continuous rings positioned at opposing ends of the core 1428. The first contrast element 1432 can be at or around a first end 1436a of the core 1428, and the second contrast element 1434 can be at or around a second end 1436b of the core 1428. The continuous rings shown in FIGS. 14A-B have substantially the same diameter and thickness. The first and second contrast elements 1432 and 1434, however, can have other configurations and/or be in other locations relative to the core 1428 in other embodiments. For example, the first and second contrast elements 1432 and 1434 can be rings with different diameters and/or thicknesses.

The radiographic centroid of the image produced by the imaging element 1430 does not need to be absolutely coincident with the magnetic centroid $M_c$, but rather the radiographic centroid and the magnetic centroid should be within an acceptable range. For example, the radiographic centroid $R_c$ can be considered to be at least approximately coincident with the magnetic centroid $M_c$ when the offset between the centroids is less than approximately 5 mm. In more stringent applications, the magnetic centroid $M_c$ and the radiographic centroid $R_c$ are considered to be at least substantially coincident with each other when the offset between the centroids is 2 mm, or less than 1 mm. In other applications, the magnetic centroid $M_c$ is at least approximately coincident with the radiographic centroid $R_c$ when the centroids are spaced apart by a distance not greater than half the length of the magnetic transponder 1420 and/or the marker 1400.

The imaging element 1430 can be made from a material and configured appropriately to absorb a high fraction of incident photons of a radiation beam used for producing the radiographic image. For example, when the imaging radiation has high acceleration voltages in the megavoltage range, the imaging element 1430 is made from, at least in part, high density materials with sufficient thickness and cross-sectional area to absorb enough of the photon fluence incident on the imaging element to be visible in the resulting radiograph. Many high energy beams used for therapy have acceleration voltages of 6 MV-25 MV, and these beams are often used to produce radiographic images in the 5 MV-10 MV range, or more specifically in the 6 MV-8 MV range. As such, the imaging element 1430 can be made from a material that is sufficiently absorbent of incident photon fluence to be visible in an image produced using a beam with an acceleration voltage of 5 MV-10 MV, or more specifically an acceleration voltage of 6 MV-8 MV.

Several specific embodiments of imaging elements 1430 can be made from gold, tungsten, platinum and/or other high density metals. In these embodiments the imaging element 1430 can be composed of materials having a density of 19.25 g/cm3 (density of tungsten) and/or a density of approximately 21.4 g/cm3 (density of platinum). Many embodiments of the imaging element 1430 accordingly have a density not less than 19 g/cm3. In other embodiments, however, the material(s) of the imaging element 1430 can have a substantially lower density. For example, imaging elements with lower density materials are suitable for applications that use lower energy radiation to produce radiographic images. Moreover, the first and second contrast elements 1432 and 1434 can be composed of different materials such that the first contrast element 1432 can be made from a first material and the second contrast element 1434 can be made from a second material.

Referring to FIG. 14B, the marker 1400 can further include a module 1440 at an opposite end of the core 1428 from the capacitor 1426. In the embodiment of the marker 1400 shown in FIG. 14B, the module 1440 is configured to be symmetrical with respect to the capacitor 1426 to enhance the symmetry of the radiographic image. As with the first and second contrast elements 1432 and 1434, the module 1440 and the capacitor 1426 are arranged such that the magnetic centroid of the marker is at least approximately coincident with the radiographic centroid of the marker 1400. The module 1440 can be another capacitor that is identical to the capacitor 1426, or the module 1440 can be an electrically inactive element. Suitable electrically inactive modules include ceramic blocks shaped like the capacitor 1426 and located with respect to the coil 1422, the core 1428 and the imaging element 1430 to be symmetrical with each other. In still other embodiments the module 1440 can be a different type of electrically active element electrically coupled to the magnetic transponder 1420.

One specific process of using the marker involves imaging the marker using a first modality and then tracking the target of the patient and/or the marker using a second modality. For example, the location of the marker relative to the target can be determined by imaging the marker and the target using radiation. The marker and/or the target can then be localized and tracked using the magnetic field generated by the marker in response to an excitation energy.

Figure 14C:
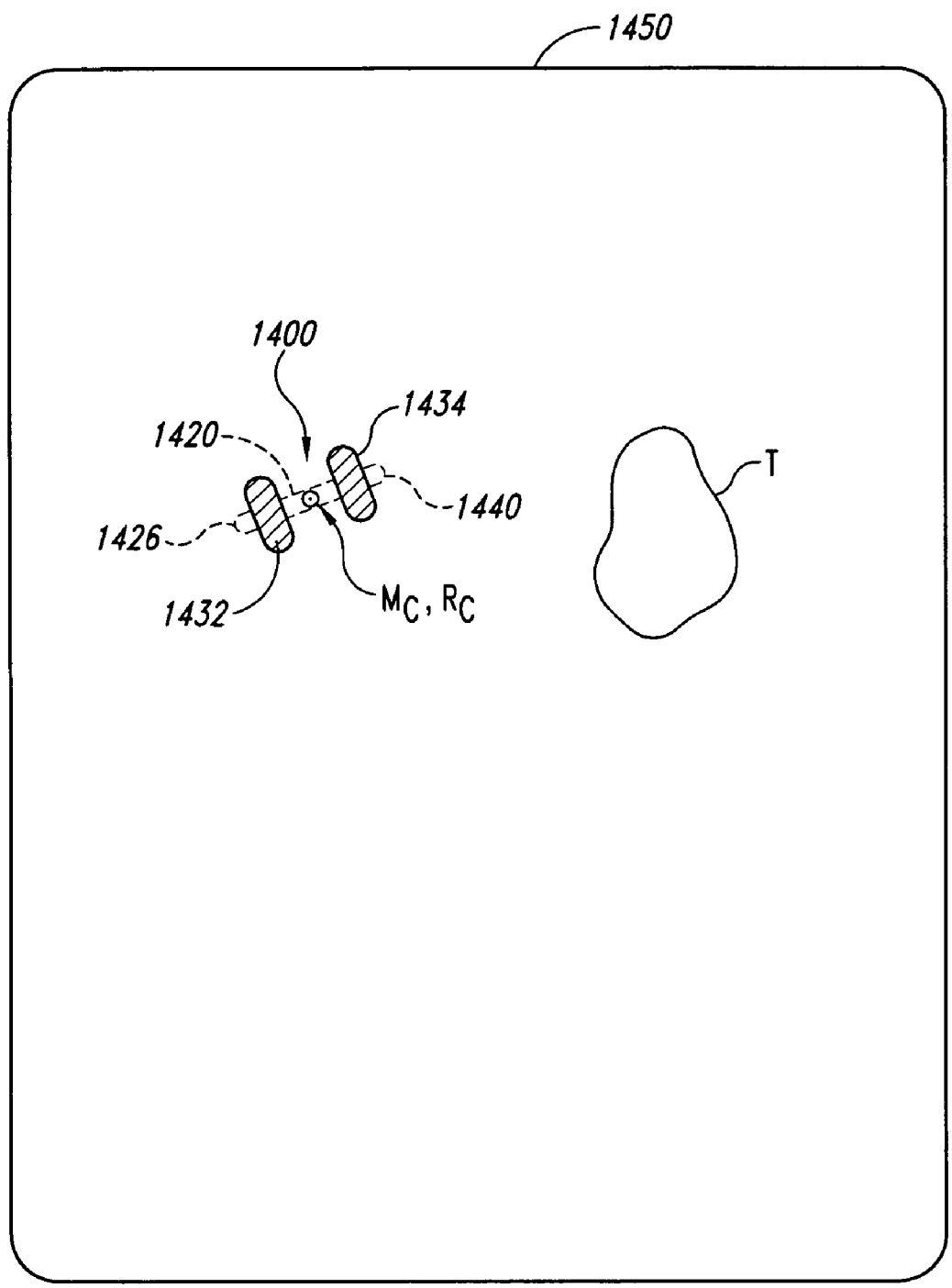
FIG. 14C is an illustration of a radiographic image of the marker of FIGS. 14A-14B.

The marker 1400 shown in FIGS. 14A-B is expected to provide an enhanced radiographic image compared to conventional magnetic markers for more accurately determining the relative position between the marker and the target of a patient. FIG. 14C, for example, illustrates a radiographic image 1450 of the marker 1400 and a target T of the patient. The first and second contrast elements 1432 and 1434 are expected to be more distinct in the radiographic image 1450 because they can be composed of higher density materials than the components of the magnetic transponder 1420. The first and second contrast elements 1432 and 1434 can accordingly appear as bulbous ends of a dumbbell shape in applications in which the components of the magnetic transponder 1420 are visible in the image. In certain megavolt applications, the components of the magnetic transponder 1420 may not appear at all on the radiographic image 1450 such that the first and second contrast elements 1432 and 1434 will appear as distinct regions that are separate from each other. In either embodiment, the first and second contrast elements 1432 and 1434 provide a reference frame in which the radiographic centroid $R_c$ of the marker 1400 can be located in the image 1450. Moreover, because the imaging element 1430 is configured so that the radiographic centroid $R_c$ is at least approximately coincident with the magnetic centroid $M_c$, the relative offset or position between the target T and the magnetic centroid $M_c$ can be accurately determined using the marker 1400. The embodiment of the marker 1400 illustrated in FIGS. 14A-C, therefore, is expected to mitigate errors caused by incorrectly estimating the radiographic and magnetic centroids of markers in radiographic images.

Figure 15A:
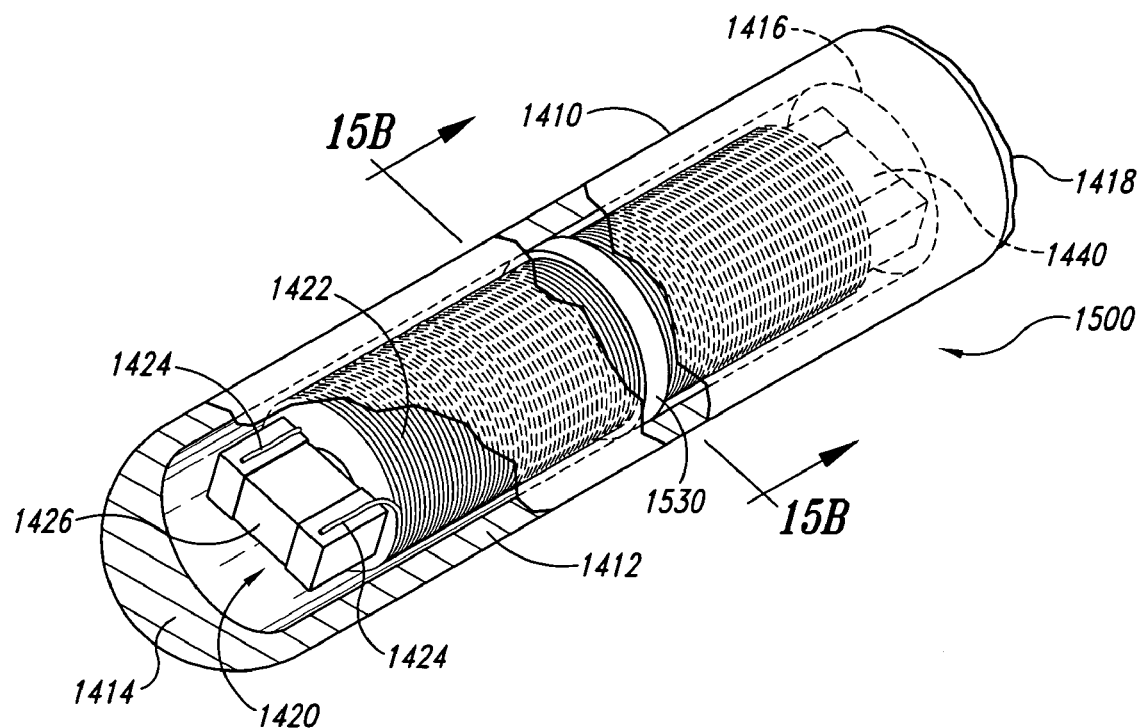
FIG. 15A is an isometric view of a marker for use with a localization system in accordance with another embodiment of the invention.
Figure 15B:
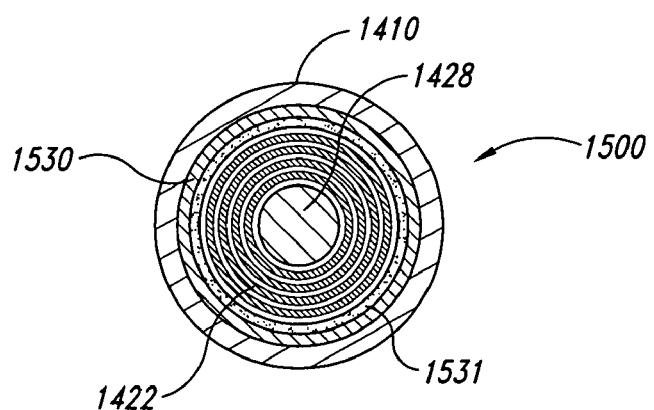
FIG. 15B is a cross-sectional view of the marker of FIG. 15A taken along line 15B-15B.

FIG. 15A is an isometric view of a marker 1500 with a cut-away portion to illustrate internal components, and FIG. 15B is a cross-sectional view of the marker 1500 taken along line 15B-15B of FIG. 15A. The marker 1500 is similar to the marker 1400 shown above in FIG. 14A, and thus like reference numbers refer to like components. The marker 1500 differs from the marker 1400 in that the marker 1500 includes an imaging element 1530 defined by a single contrast element. The imaging element 1530 is generally configured relative to the magnetic transponder 1420 so that the radiographic centroid of the marker 1500 is at least approximately coincident with the magnetic centroid of the magnetic transponder 1420. The imaging element 1530, more specifically, is a ring extending around the coil 1422 at a medial region of the magnetic transponder 1420. The imaging element 1530 can be composed of the same materials described above with respect to the imaging element 1430 in FIGS. 14A-B. The imaging element 1530 can have an inner diameter that is approximately equal to the outer diameter of the coil 1422, and an outer diameter within the casing 1410. As shown in FIG. 15B, however, a spacer 1531 can be between the inner diameter of the imaging element 1530 and the outer diameter of the coil 1422.

The marker 1500 is expected to operate in a manner similar to the marker 1400 described above. The marker 1500, however, does not have two separate contrast elements that provide two distinct, separate points in a radiographic image. The imaging element 1530 is still highly useful in that it identifies the radiographic centroid of the marker 1500 in a radiographic image, and it can be configured so that the radiographic centroid of the marker 1500 is at least approximately coincident with the magnetic centroid of the magnetic transponder 1420.

Figure 16A:
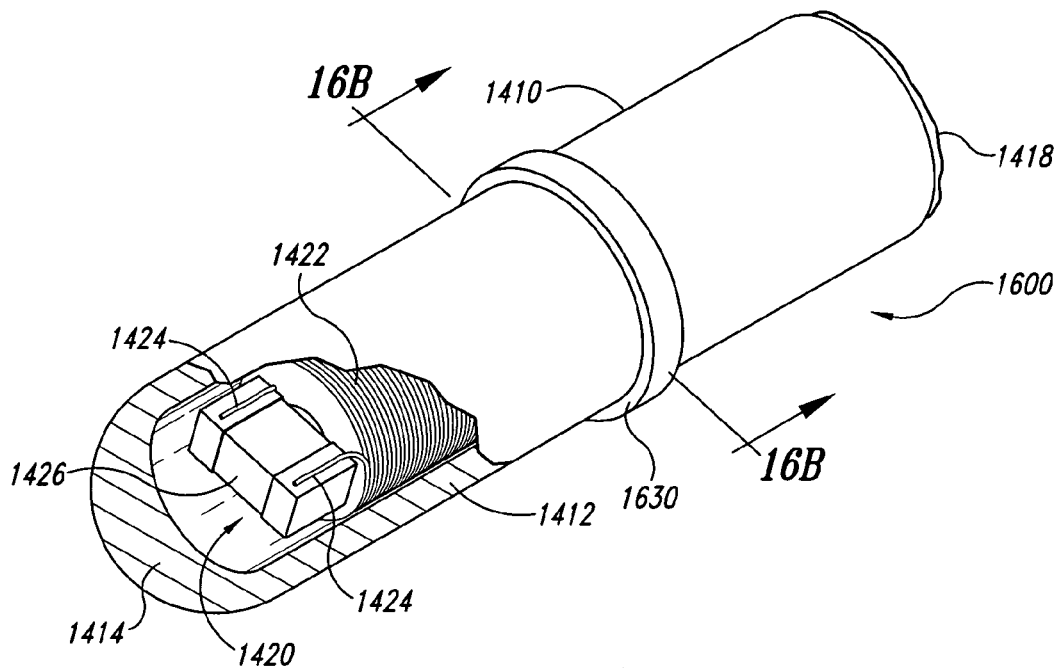
FIG. 16A is an isometric view of a marker for use with a localization system in accordance with another embodiment of the invention.
Figure 16B:
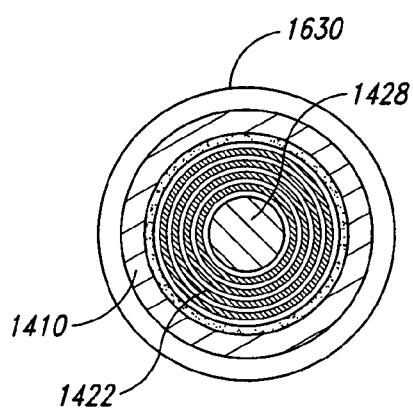
FIG. 16B is a cross-sectional view of the marker of FIG. 16A taken along line 16B-16B.

FIG. 16A is an isometric view of a marker 1600 having a cut-away portion, and FIG. 16B is a cross-sectional view of the marker 1600 taken along line 16B-16B of FIG. 16A. The marker 1600 is substantially similar to the marker 1500 shown in FIGS. 15A-B, and thus like reference numbers refer to like components in FIGS. 14A-16B. The imaging element 1630 can be a high density ring configured relative to the magnetic transponder 1420 so that the radiographic centroid of the marker 1600 is at least approximately coincident with the magnetic centroid of the magnetic transponder 1420. The marker 1600, more specifically, includes an imaging element 1630 around the casing 1410. The marker 1600 is expected to operate in much the same manner as the marker 1500 shown in FIGS. 15A-B.

Figure 17:
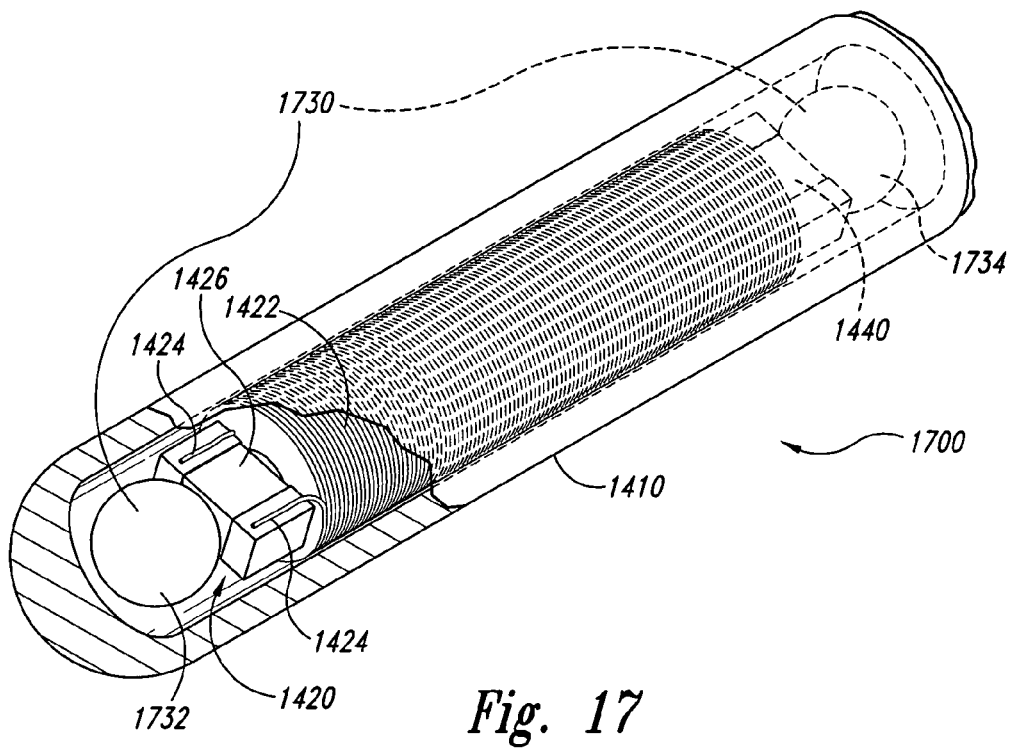
FIG. 17 is an isometric view of a marker for use with a localization system in accordance with another embodiment of the invention.

FIG. 17 is an isometric view with a cut-away portion illustrating a marker 1700 in accordance with another embodiment of the invention. The marker 1700 is similar to the marker 1400 shown in FIGS. 14A-C, and thus like reference numbers refer to like components in these Figures. The marker 1700 has an imaging element 1730 including a first contrast element 1732 at one end of the magnetic transponder 1420 and a second contrast element 1734 at another end of the magnetic transponder 1420. The first and second contrast elements 1732 and 1734 are spheres composed of suitable high density materials. The contrast elements 1732 and 1734, for example, can be composed of gold, tungsten, platinum or other suitable high-density materials for use in radiographic imaging. The marker 1700 is expected to operate in a manner similar to the marker 1400, as described above.

Figure 18:
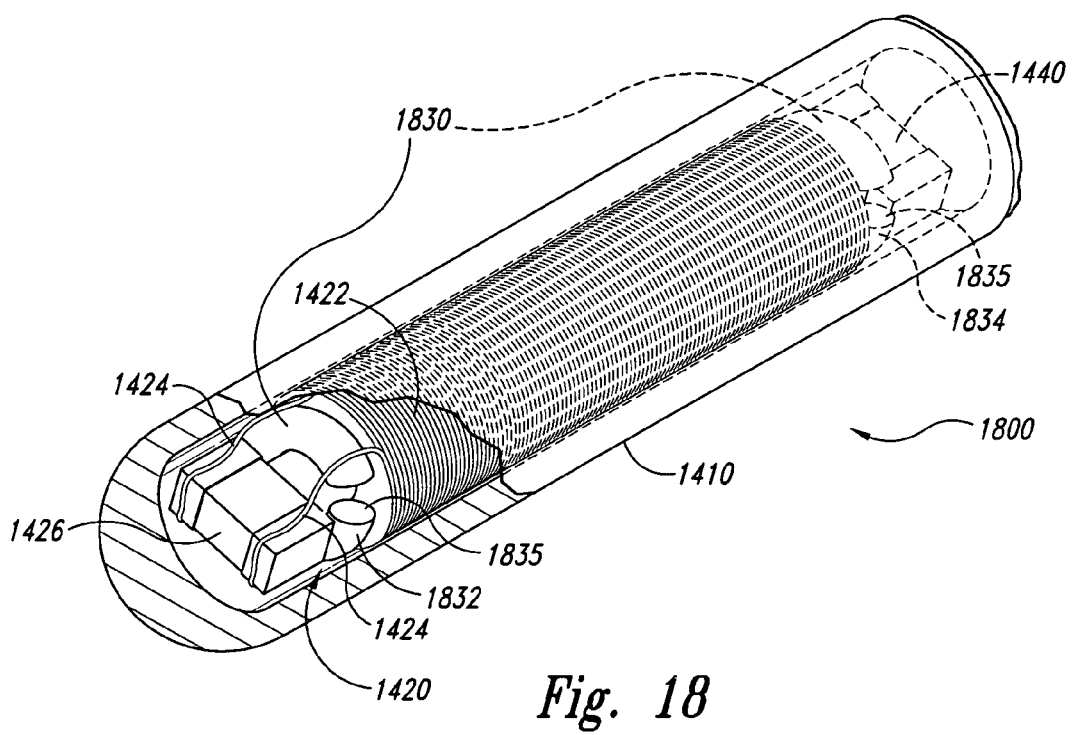
FIG. 18 is an isometric view of a marker for use with a localization system in accordance with yet another embodiment of the invention.

FIG. 18 is an isometric view with a cut-away portion of a marker 1800 in accordance with yet another embodiment of the invention. The marker 1800 is substantially similar to the markers 1400 and 1700 shown in FIGS. 14A and 17, and thus like reference numbers refer to like components in these Figures. The marker 1800 includes an imaging element 1830 including a first contrast element 1832 and a second contrast element 1834. The first and second contrast elements 1832 and 1834 can be positioned proximate to opposing ends of the magnetic transponder 1420. The first and second contrast elements 1832 and 1834 can be discontinuous rings having a gap 1835 to mitigate eddy currents. The contrast elements 1832 and 1834 can be composed of the same materials as described above with respect to the contrast elements of other imaging elements in accordance with other embodiments of the invention.

Additional embodiments of markers in accordance with the invention can include imaging elements incorporated into or otherwise integrated with the casing 1410, the core 1428 (FIG. 14B) of the magnetic transponder 1420, and/or the adhesive 1429 (FIG. 14B) in the casing. For example, particles of a high density material can be mixed with ferrite and extruded to form the core 1428. Alternative embodiments can mix particles of a high density material with glass or another material to form the casing 1410, or coat the casing 1410 with a high-density material. In still other embodiments, a high density material can be mixed with the adhesive 1429 and injected into the casing 1410. Any of these embodiments can incorporate the high density material into a combination of the casing 1410, the core 1428 and/or the adhesive 1429. Suitable high density materials can include tungsten, gold and/or platinum as described above.

The markers described above with reference to FIGS. 14A-18 can be used for the markers 40 in the localization system 10 (FIGS. 7-13). The localization system 10 can have several markers with the same type of imaging elements, or markers with different imaging elements can be used with the same instrument. Several additional details of these markers and other embodiments of markers are described in U.S. application Ser. Nos. 10/334,698 and 10/746,888, which are incorporated herein by reference. For example, the markers may not have any imaging elements for applications with lower energy radiation, or the markers may have reduced volumes of ferrite and metals to mitigate issues with MRI imaging as set forth in U.S. application Ser. No. 10/334,698.

2. Localization Systems

Figure 19:
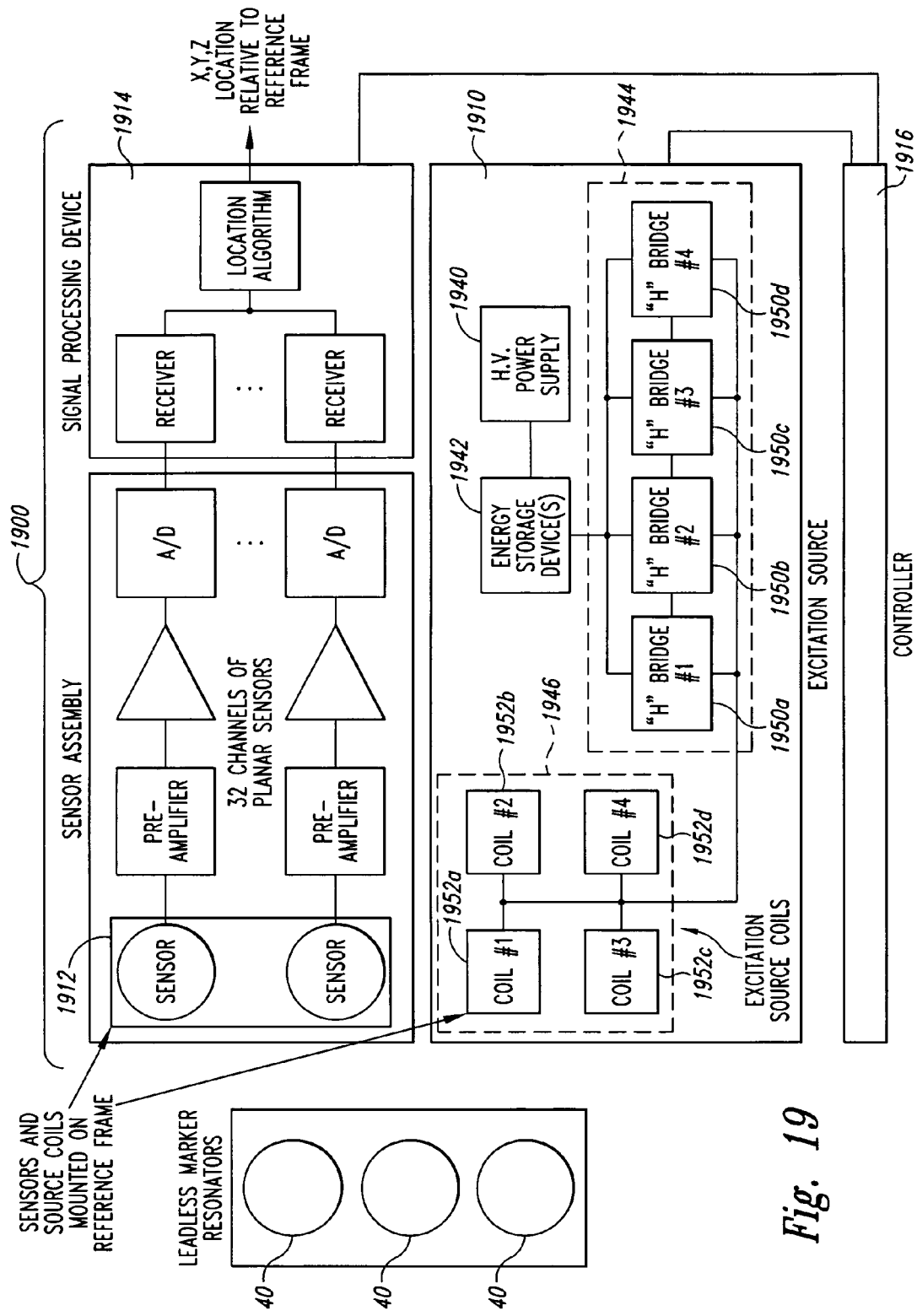
FIG. 19 is a schematic block diagram of a localization system for use in tracking a target in accordance with an embodiment of the invention.

FIG. 19 is a schematic block diagram of a localization system 1900 for determining the absolute location of the markers 40 (shown schematically) relative to a reference frame. The localization system 1900 includes an excitation source 1910, a sensor assembly 1912, a signal processor 1914 operatively coupled to the sensor assembly 1912, and a controller 1916 operatively coupled to the excitation source 1910 and the signal processor 1914. The excitation source 1910 is one embodiment of the excitation source 60 described above with reference to FIG. 9; the sensor assembly 1912 is one embodiment of the sensor assembly 70 described above with reference to FIG. 9; and the controller 1916 is one embodiment of the controller 80 described above with reference to FIG. 9.

The excitation source 1910 is adjustable to generate a magnetic field having a waveform with energy at selected frequencies to match the resonant frequencies of the markers 40. The magnetic field generated by the excitation source 1910 energizes the markers at their respective frequencies. After the markers 40 have been energized, the excitation source 1910 is momentarily switched to an "off" position so that the pulsed magnetic excitation field is terminated while the markers wirelessly transmit the location signals. This allows the sensor assembly 1912 to sense the location signals from the markers 40 without measurable interference from the significantly more powerful magnetic field from the excitation source 1910. The excitation source 1910 accordingly allows the sensor assembly 1912 to measure the location signals from the markers 40 at a sufficient signal-to-noise ratio so that the signal processor 1914 or the controller 1916 can accurately calculate the absolute location of the markers 40 relative to a reference frame.

a. Excitation Sources

Referring still to FIG. 19, the excitation source 1910 includes a high voltage power supply 1940, an energy storage device 1942 coupled to the power supply 1940, and a switching network 1944 coupled to the energy storage device 1942. The excitation source 1910 also includes a coil assembly 1946 coupled to the switching network 1944. In one embodiment, the power supply 1940 is a 500 volt power supply, although other power supplies with higher or lower voltages can be used. The energy storage device 1942 in one embodiment is a high voltage capacitor that can be charged and maintained at a relatively constant charge by the power supply 1940. The energy storage device 1942 alternately provides energy to and receives energy from the coils in the coil assembly 1946.

The energy storage device 1942 is capable of storing adequate energy to reduce voltage drop in the energy storage device while having a low series resistance to reduce power losses. The energy storage device 1942 also has a low series inductance to more effectively drive the coil assembly 1946. Suitable capacitors for the energy storage device 1942 include aluminum electrolytic capacitors used in flash energy applications. Alternative energy storage devices can also include NiCd and lead acid batteries, as well as alternative capacitor types, such as tantalum, film, or the like.

The switching network 1944 includes individual H-bridge switches 1950 (identified individually by reference numbers 1950a-d), and the coil assembly 1946 includes individual source coils 1952 (identified individually by reference numbers 1952a-d). Each H-bridge switch 1950 controls the energy flow between the energy storage device 1942 and one of the source coils 1952. For example, H-bridge switch #1 1950a independently controls the flow of the energy to/from source coil #1 1952a, H-bridge switch #2 1950b independently controls the flow of the energy to/from source coil #2 1952b, H-bridge switch #3 1950c independently controls the flow of the energy to/from source coil #3 1952c, and H-bridge switch #4 1950d independently controls the flow of the energy to/from source coil #4 1952d. The switching network 1944 accordingly controls the phase of the magnetic field generated by each of the source coils 1952a-d independently. The H-bridges 1950 can be configured so that the electrical signals for all the source coils 1952 are in phase, or the H-bridge switches 1950 can be configured so that one or more of the source coils 1952 are 180° out of phase. Furthermore, the H-bridge switches 1950 can be configured so that the electrical signals for one or more of the source coils 1952 are between 0 and 180° out of phase to simultaneously provide magnetic fields with different phases.

The source coils 1952 can be arranged in a coplanar array that is fixed relative to the reference frame. Each source coil 1952 can be a square, planar winding arranged to form a flat, substantially rectilinear coil. The source coils 1952 can have other shapes and other configurations in different embodiments. In one embodiment, the source coils 1952 are individual conductive lines formed in a stratum of a printed circuit board, or windings of a wire in a foam frame. Alternatively, the source coils 1952 can be formed in different substrates or arranged so that two or more of the source coils are not planar with each other. Additionally, alternate embodiments of the invention may have fewer or more source coils than illustrated in FIG. 19.

The selected magnetic fields from the source coils 1952 combine to form an adjustable excitation field that can have different three-dimensional shapes to excite the markers 40 at any spatial orientation within an excitation volume. When the planar array of the source coils 1952 is generally horizontal, the excitation volume is positioned above an area approximately corresponding to the central region of the coil assembly 1946. The excitation volume is the three-dimensional space adjacent to the coil assembly 1946 in which the strength of the magnetic field is sufficient to adequately energize the markers 40.

Figure 20:
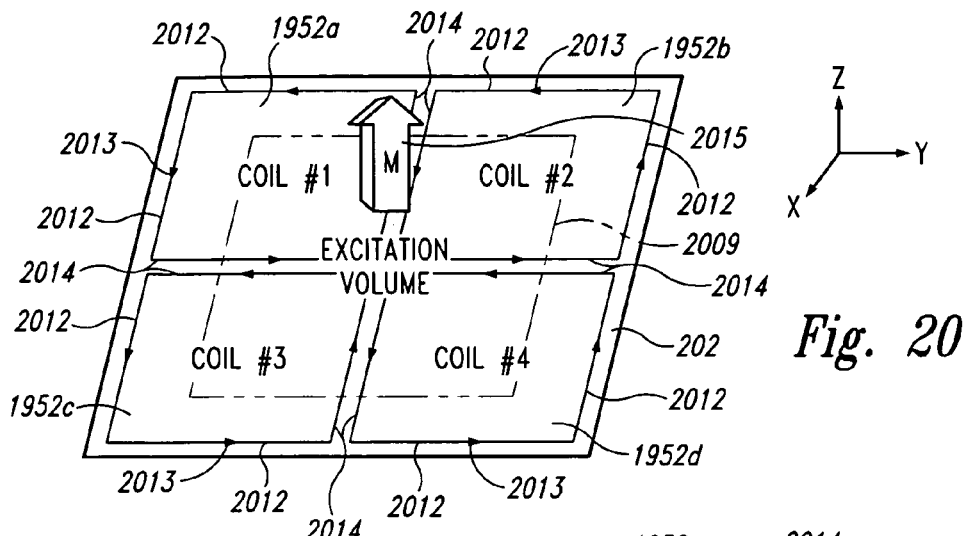
FIG. 20 is a schematic view of an array of coplanar source coils carrying electrical signals in a first combination of phases to generate a first excitation field.
Figure 21:
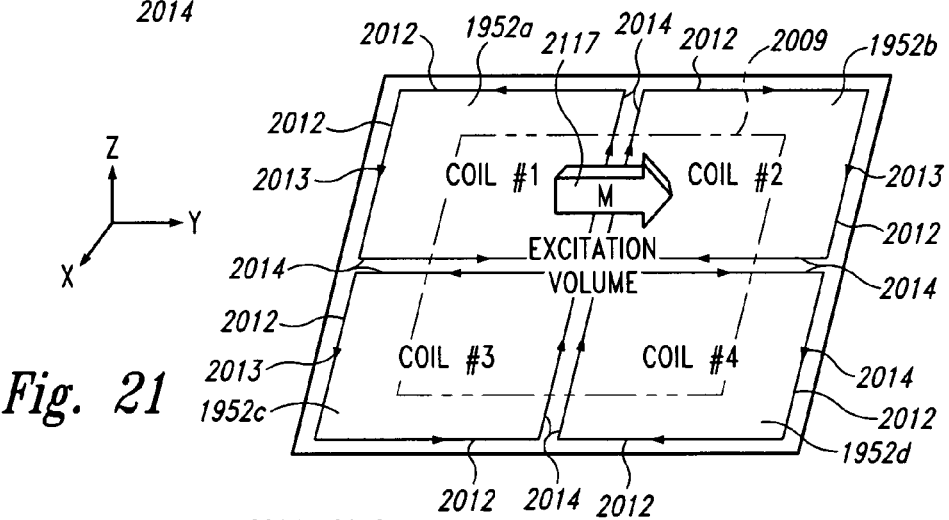
FIG. 21 is a schematic view of an array of coplanar source coils carrying electrical signals in a second combination of phases to generate a second excitation field.
Figure 22:
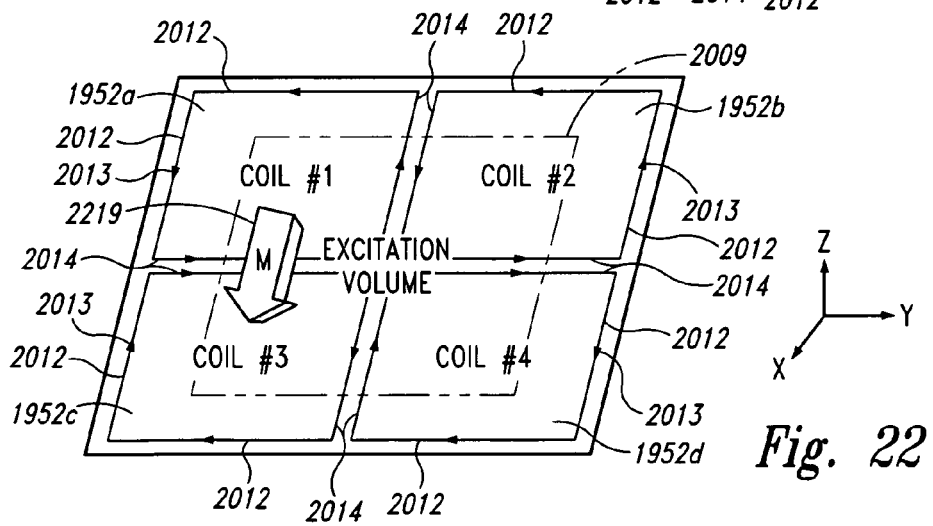
FIG. 22 is a schematic view of an array of coplanar source coils carrying electrical signals in a third combination of phases to generate a third excitation field.

FIGS. 20-22 are schematic views of a planar array of the source coils 1952 with the alternating electrical signals provided to the source coils in different combinations of phases to generate excitation fields about different axes relative to the illustrated XYZ coordinate system. Each source coil 1952 has two outer sides 2012 and two inner sides 2014. Each inner side 2014 of one source coil 1952 is immediately adjacent to an inner side 2014 of another source coil 1952, but the outer sides 2012 of all the source coils 1952 are not adjacent to any other source coil 1952.

In the embodiment of FIG. 20, all the source coils 1952a-d simultaneously receive an alternating electrical signals in the same phase. As a result, the electrical current flows in the same direction through all the source coils 1952a-d such that a direction 2013 of the current flowing along the inner sides 2014 of one source coil (e.g., source coil 1952a) is opposite to the direction 2013 of the current flowing along the inner sides 2014 of the two adjacent source coils (e.g., source coils 1952c and 1952d). The magnetic fields generated along the inner sides 2014 accordingly cancel each other out so that the magnetic field is effectively generated from the current flowing along the outer sides 2012 of the source coils. The resulting excitation field formed by the combination of the magnetic fields from the source coils 1952a-d shown in FIG. 20 has a magnetic moment 2015 generally in the Z direction within an excitation volume 1109. This excitation field energizes markers parallel to the Z-axis or markers positioned with an angular component along the Z-axis (i.e., not orthogonal to the Z-axis).

FIG. 21 is a schematic view of the source coils 1952a-d with the alternating electrical signals provided in a second combination of phases to generate a second excitation field with a different spatial orientation. In this embodiment, source coils 1952a and 1952c are in phase with each other, and source coils 1952b and 1952d are in phase with each other. However, source coils 1952a and 1952c are 180 degrees out of phase with source coils 1952b and 1952d. The magnetic fields from the source coils 1952a-d combine to generate an excitation field having a magnetic moment 2117 generally in the Y direction within the excitation volume 2009. Accordingly, this excitation field energizes markers parallel to the Y-axis or markers positioned with an angular component along the Y-axis.

FIG. 22 is a schematic view of the source coils 1952a-d with the alternating electrical signals provided in a third combination of phases to generate a third excitation field with a different spatial orientation. In this embodiment, source coils 1952a and 1952b are in phase with each other, and source coils 1952c and 1952d are in phase with each other. However, source coils 1952a and 1952b are 180 degrees out of phase with source coils 1952c and 1952d. The magnetic fields from the source coils 1952a-d combine to generate an excitation field having a magnetic moment 2219 in the excitation volume 2009 generally in the direction of the X-axis. Accordingly, this excitation field energizes markers parallel to the X-axis or markers positioned with an angular component along the X-axis.

Figure 23:
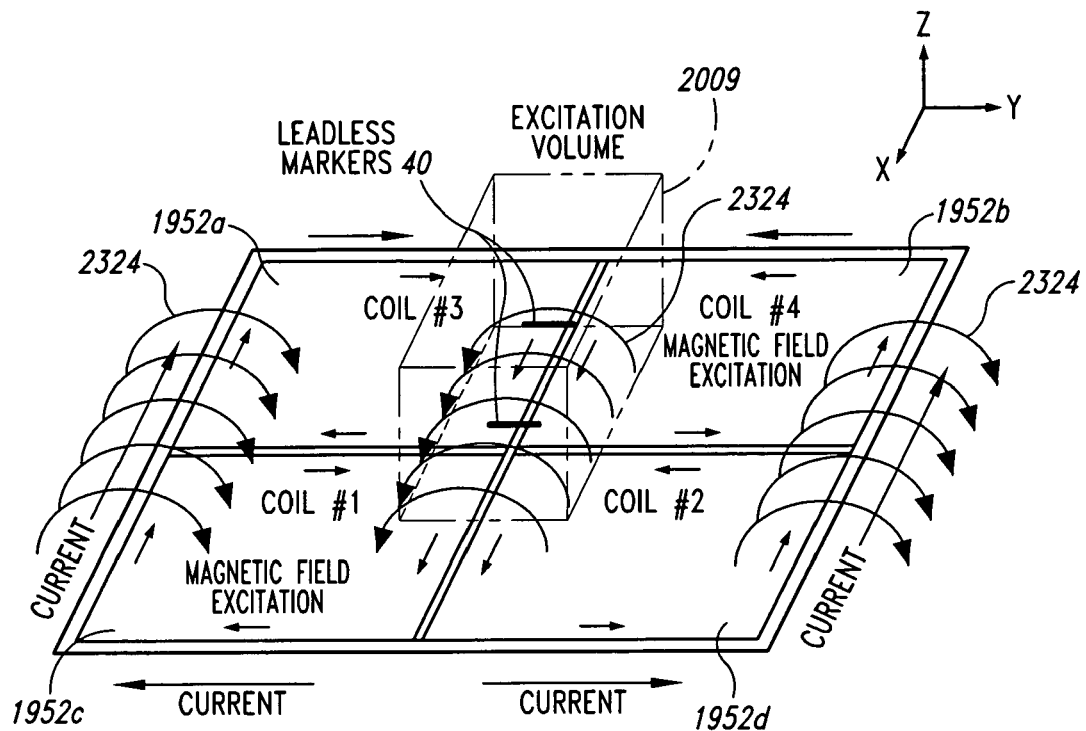
FIG. 23 is a schematic view of an array of coplanar source coils illustrating a magnetic excitation field for energizing markers in a first spatial orientation.

FIG. 23 is a schematic view of the source coils 1952a-d illustrating the current flow to generate an excitation field 2324 for energizing markers 40 with longitudinal axes parallel to the Y-axis. The switching network 1944 (FIG. 19) is configured so that the phases of the alternating electrical signals provided to the source coils 1952*a-d* are similar to the configuration of FIG. 21. This generates the excitation field 2324 with a magnetic moment in the Y direction to energize the markers 40.

Figure 24:
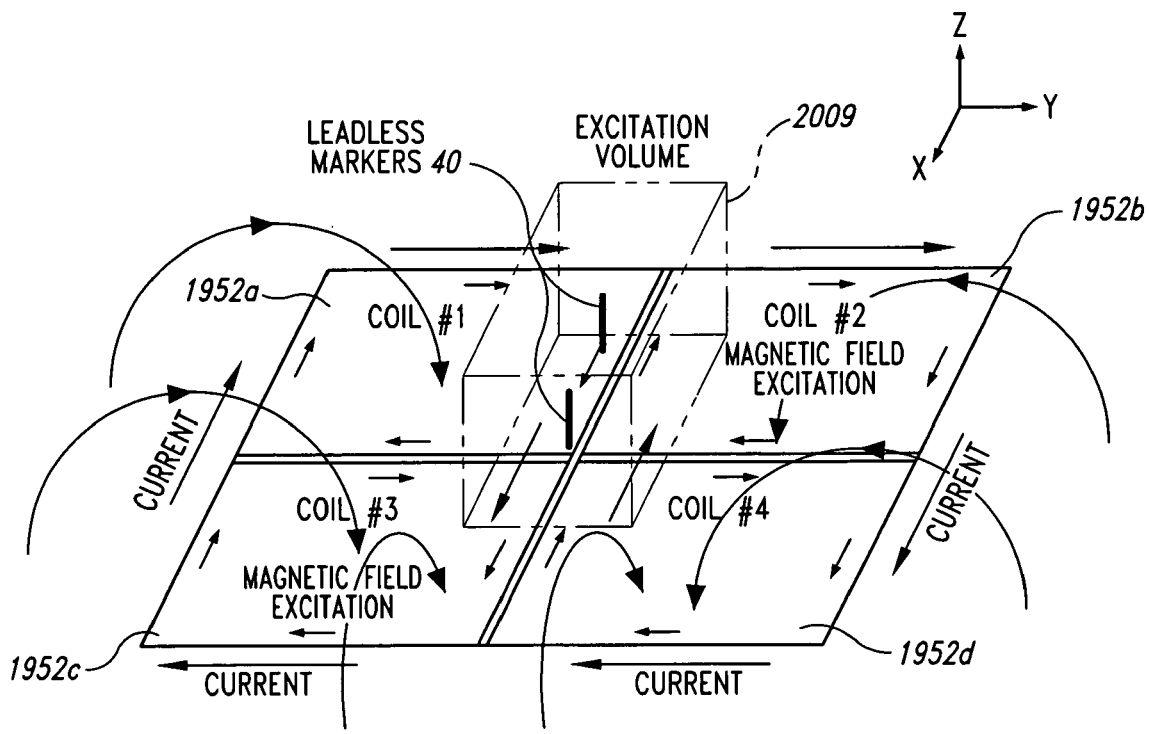
FIG. 24 is a schematic view of an array of coplanar source coils illustrating a magnetic excitation field for energizing markers in a second spatial orientation.

FIG. 24 further illustrates the ability to spatially adjust the excitation field in a manner that energizes any of the markers 40 at different spatial orientations. In this embodiment, the switching network 1944 (FIG. 19) is configured so that the phases of the alternating electrical signals provided to the source coils 1952*a-d* are similar to the configuration shown in FIG. 20. This produces an excitation field with a magnetic moment in the Z direction that energizes markers 40 with longitudinal axes parallel to the Z-axis.

The spatial configuration of the excitation field in the excitation volume 2009 can be quickly adjusted by manipulating the switching network to change the phases of the electrical signals provided to the source coils 1952*a-d*. As a result, the overall magnetic excitation field can be changed to be oriented in either the X, Y or Z directions within the excitation volume 2009. This adjustment of the spatial orientation of the excitation field reduces or eliminates blind spots in the excitation volume 2009. Therefore, the markers 40 within the excitation volume 2009 can be energized by the source coils 1952*a-d* regardless of the spatial orientations of the leadless markers.

In one embodiment, the excitation source 1910 is coupled to the sensor assembly 1912 so that the switching network 1944 (FIG. 19) adjusts orientation of the pulsed generation of the excitation field along the X, Y, and Z axes depending upon the strength of the signal received by the sensor assembly. If the location signal from a marker 40 is insufficient, the switching network 1944 can automatically change the spatial orientation of the excitation field during a subsequent pulsing of the source coils 1952*a-d* to generate an excitation field with a moment in the direction of a different axis or between axes. The switching network 1944 can be manipulated until the sensor assembly 1912 receives a sufficient location signal from the marker.

The excitation source 1910 illustrated in FIG. 19 alternately energizes the source coils 1952*a-d* during an excitation phase to power the markers 40, and then actively de-energizes the source coils 1952*a-d* during a sensing phase in which the sensor assembly 1912 senses the decaying location signals wirelessly transmitted by the markers 40. To actively energize and de-energize the source coils 1952*a-d*, the switching network 1944 is configured to alternatively transfer stored energy from the energy storage device 1942 to the source coils 1952*a-d*, and to then re-transfer energy from the source coils 1952*a-d* back to the energy storage device 1942. The switching network 1944 alternates between first and second "on" positions so that the voltage across the source coils 1952 alternates between positive and negative polarities. For example, when the switching network 1944 is switched to the first "on" position, the energy in the energy storage device 1942 flows to the source coils 1952*a-d*. When the switching network 1944 is switched to the second "on" position, the polarity is reversed such that the energy in the source coils 1952*a-d* is actively drawn from the source coils 1952*a-d* and directed back to the energy storage device 1942. As a result, the energy in the source coils 1952*a-d* is quickly transferred back to the energy storage device 1942 to abruptly terminate the excitation field transmitted from the source coils 1952*a-d* and to conserve power consumed by the energy storage device 1942. This removes the excitation energy from the environment so that the sensor assembly 1912 can sense the location signals from the markers 40 without interference from the significantly larger excitation energy from the excitation source 1910. Several additional details of the excitation source 1910 and alternate embodiments are disclosed in U.S. patent application Ser. No. 10/213,980 filed on Aug. 7, 2002, and now U.S. Pat. No. 6,822,570, which is incorporated by reference herein in its entirety.

b. Sensor Assemblies

Figure 25A:
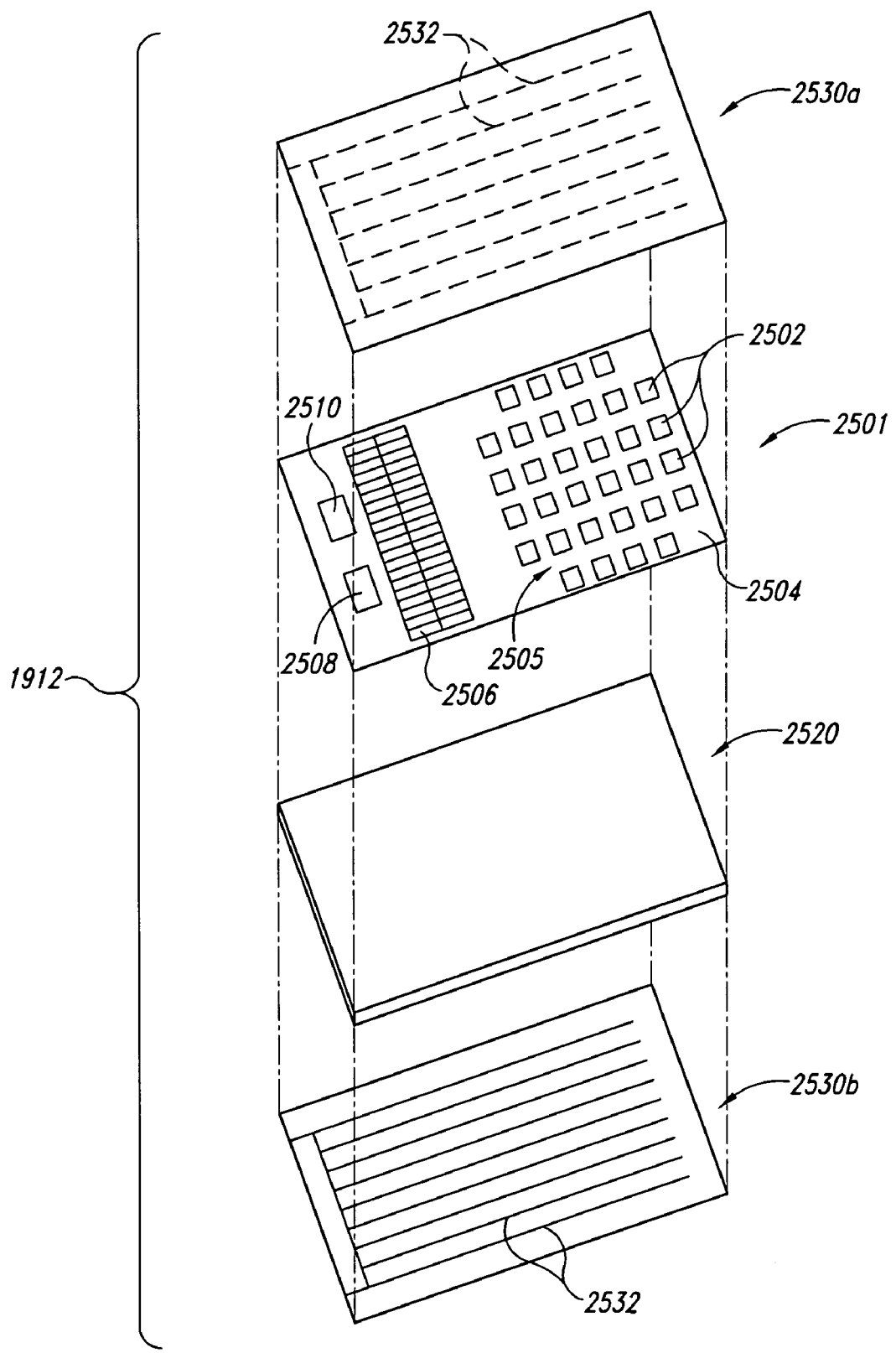
FIG. 25A is an exploded isometric view showing individual components of a sensor assembly for use with a localization system in accordance with an embodiment of the invention.

FIG. 25A is an exploded isometric view showing several components of the sensor assembly 1912 for use in the localization system 1900 (FIG. 19). The sensor assembly 1912 includes a sensing unit 2501 having a plurality of coils 2502 formed on or carried by a panel 2504. The coils 2502 can be field sensors or magnetic flux sensors arranged in a sensor array 2505.

The panel 2504 may be a substantially non-conductive material, such as a sheet of KAPTON® produced by DuPont. KAPTON® is particularly useful when an extremely stable, tough, and thin film is required (such as to avoid radiation beam contamination), but the panel 2504 may be made from other materials and have other configurations. For example, FR4 (epoxy-glass substrates), GETEK or other Teflon-based substrates, and other commercially available materials can be used for the panel 2504. Additionally, although the panel 2504 may be a flat, highly planar structure, in other embodiments, the panel may be curved along at least one axis. In either embodiment, the field sensors (e.g., coils) are arranged in a locally planar array in which the plane of one field sensor is at least substantially coplanar with the planes of adjacent field sensors. For example, the angle between the plane defined by one coil relative to the planes defined by adjacent coils can be from approximately 0° to 10°, and more generally is less than 5°. In some circumstances, however, one or more of the coils may be at an angle greater than 100 relative to other coils in the array.

The sensor assembly 1912 shown in FIG. 25A can optionally include a core 2520 laminated to the panel 2504. The core 2520 can be a support member made from a rigid material, or the core 2520 can be a low density foam, such as a closed-cell Rohacell foam. The core 2520 is preferably a stable layer that has a low coefficient of thermal expansion so that the shape of the sensor assembly 1912 and the relative orientation between the coils 2502 remain within a defined range over an operating temperature range.

The sensor assembly 1912 can further include a first exterior cover 2530*a* on one side of the sensing subsystem and a second exterior cover 2530*b* on an opposing side. The first and second exterior covers 2530*a-b* can be thin, thermally stable layers, such as Kevlar or Thermount films. Each of the first and second exterior covers 2530*a-b* can include electric shielding 2532 to block undesirable external electric fields from reaching the coils 2502. The electric shielding 2532 can be a plurality of parallel legs of gold-plated, copper strips to define a comb-shaped shield in a configuration commonly called a Faraday shield. It will be appreciated that the shielding can be formed from other materials that are suitable for shielding. The electric shielding can be formed on the first and second exterior covers using printed circuit board manufacturing technology or other techniques.

The panel 2504 with the coils 2502 is laminated to the core 2520 using a pressure sensitive adhesive or another type of adhesive. The first and second exterior covers 2530*a-b* are similarly laminated to the assembly of the panel 2504 and the core 2520. The laminated assembly forms a rigid structure that fixedly retains the arrangement of the coils 2502 in a defined configuration over a large operating temperature range. As such, the sensor assembly 1912 does not substantially deflect across its surface during operation. The sensor assembly 1912, for example, can retain the array of coils 2502 in the fixed position with a deflection of no greater than ±0.5 mm, and in some cases no more than ±0.3 mm. The stiffness of the sensing subsystem provides very accurate and repeatable monitoring of the precise location of leadless markers in real time.

In still another embodiment, the sensor assembly 1912 can further include a plurality of source coils that are a component of the excitation source 1910. One suitable array combining the sensor assembly 1912 with source coils is disclosed in U.S. patent application Ser. No. 10/334,700, entitled PANEL-TYPE SENSOR/SOURCE ARRAY ASSEMBLY, filed on Dec. 30, 2002, which is herein incorporated by reference.

Figure 25B:
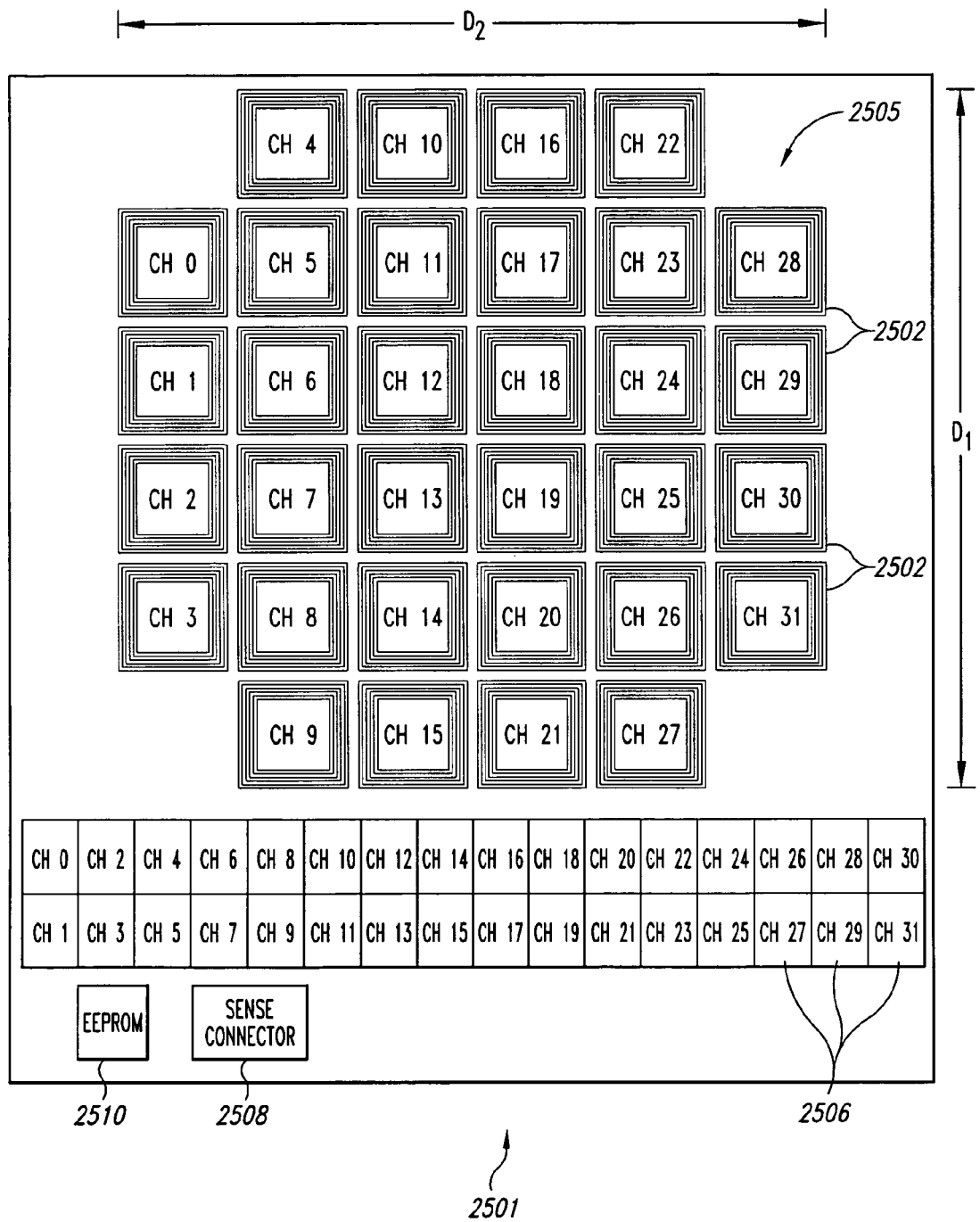
FIG. 25B is a top plan view of a sensing unit for use in the sensor assembly of FIG. 25A.

FIG. 25B further illustrates an embodiment of the sensing unit 2501. In this embodiment, the sensing unit 2501 includes 32 sensor coils 2502; each coil 2502 is associated with a separate channel 2506 (shown individually as channels "Ch 0" through "Ch 31"). The overall dimension of the panel 2504 can be approximately 40 cm by 54 cm, but the array 2505 has a first dimension D1 of approximately 40 cm and a second dimension D2 of approximately 40 cm. The array 2505 can have other sizes or other configurations (e.g., circular) in alternative embodiments. Additionally, the array 2505 can have more or fewer coils, such as 8-64 coils; the number of coils may moreover be a power of 2.

The coils 2502 may be conductive traces or depositions of copper or another suitably conductive metal formed on the panel 2504. Each coil 2502 has a trace with a width of approximately 0.15 mm and a spacing between adjacent turns within each coil of approximately 0.13 mm. The coils 2502 can have approximately 15 to 90 turns, and in specific applications each coil has approximately 40 turns. Coils with less than 15 turns may not be sensitive enough for some applications, and coils with more than 90 turns may lead to excessive voltage from the source signal during excitation and excessive settling times resulting from the coil's lower self-resonant frequency. In other applications, however, the coils 2502 can have less than 15 turns or more than 90 turns.

As shown in FIG. 25B, the coils 2502 are arranged as square spirals, although other configurations may be employed, such as arrays of circles, interlocking hexagons, triangles, etc. Such square spirals utilize a large percentage of the surface area to improve the signal to noise ratio. Square coils also simplify design layout and modeling of the array compared to circular coils; for example, circular coils could waste surface area for linking magnetic flux from the markers 40. The coils 2502 have an inner dimension of approximately 40 mm, and an outer dimension of approximately 62 mm, although other dimensions are possible depending upon applications. Sensitivity may be improved with an inner dimension as close to an outer dimension as possible given manufacturing tolerances. In several embodiments, the coils 2502 are identical to each other or at least configured substantially similarly.

The pitch of the coils 2502 in the array 2505 is a function of, at least in part, the minimum distance between the marker and the coil array. In one embodiment, the coils are arranged at a pitch of approximately 67 mm. This specific arrangement is particularly suitable when the wireless markers 40 are positioned approximately 7-27 cm from the sensor assembly 1912. If the wireless markers are closer than 7 cm, then the sensing subsystem may include sensor coils arranged at a smaller pitch. In general, a smaller pitch is desirable when wireless markers are to be sensed at a relatively short distance from the array of coils. The pitch of the coils 2502, for example, is approximately 50%-200% of the minimum distance between the marker and the array.

In general, the size and configuration of the array 2505 and the coils 2502 in the array depend on the frequency range in which they are to operate, the distance from the markers 40 to the array, the signal strength of the markers, and several other factors. Those skilled in the relevant art will readily recognize that other dimensions and configurations may be employed depending, at least in part, on a desired frequency range and distance from the markers to the coils.

The array 2505 is sized to provide a large aperture to measure the magnetic field emitted by the markers. It can be particularly challenging to accurately measure the signal emitted by an implantable marker that wirelessly transmits a marker signal in response to a wirelessly transmitted energy source because the marker signal is much smaller than the source signal and other magnetic fields in a room (e.g., magnetic fields from CRTs, etc.). The size of the array 2505 can be selected to preferentially measure the near field of the marker while mitigating interference from far field sources. In one embodiment, the array 2505 is sized to have a maximum dimension D1 or D2 across the surface of the area occupied by the coils that is approximately 100% to 300% of a predetermined maximum sensing distance that the markers are to be spaced from the plane of the coils. Thus, the size of the array 2505 is determined by identifying the distance that the marker is to be spaced apart from the array to accurately measure the marker signal, and then arrange the coils so that the maximum dimension of the array is approximately 100% to 300% of that distance. The maximum dimension of the array 2505, for example, can be approximately 200% of the sensing distance at which a marker is to be placed from the array 2505. In one specific embodiment, the marker 40 has a sensing distance of 20 cm and the maximum dimension of the array of coils 2502 is between 20 cm and 60 cm, and more specifically 40 cm.

A coil array with a maximum dimension as set forth above is particularly useful because it inherently provides a filter that mitigates interference from far field sources. As such, one aspect of several embodiments of the invention is to size the array based upon the signal from the marker so that the array preferentially measures near field sources (i.e., the field generated by the marker) and filters interference from far field sources.

The coils 2502 are electromagnetic field sensors that receive magnetic flux produced by the wireless markers 40 and in turn produce a current signal representing or proportional to an amount or magnitude of a component of the magnetic field through an inner portion or area of each coil. The field component is also perpendicular to the plane of each coil 2502. Each coil represents a separate channel, and thus each coil outputs signals to one of 32 output ports 2506. A preamplifier, described below, may be provided at each output port 2506. Placing preamplifiers (or impedance buffers) close to the coils minimizes capacitive loading on the coils, as described herein. Although not shown, the sensing unit 2501 also includes conductive traces or conductive paths routing signals from each coil 2502 to its corresponding output port 2506 to thereby define a separate channel. The ports in turn are coupled to a connector 2508 formed on the panel 2504 to which an appropriately configured plug and associated cable may be attached.

The sensing unit 2501 may also include an onboard memory or other circuitry, such as shown by electrically erasable programmable read-only memory (EEPROM) 2510. The EEPROM 2510 may store manufacturing information such as a serial number, revision number, date of manufacture, and the like. The EEPROM 2510 may also store per-channel calibration data, as well as a record of run-time. The run-time will give an indication of the total radiation dose to which the array has been exposed, which can alert the system when a replacement sensing subsystem is required.

Although shown in one plane only, additional coils or electromagnetic field sensors may be arranged perpendicular to the panel 2504 to help determine a three-dimensional location of the wireless markers 40. Adding coils or sensors in other dimensions could increase the total energy received from the wireless markers 40, but the complexity of such an array would increase disproportionately. The inventors have found that three-dimensional coordinates of the wireless markers 40 may be found using the planar array shown in FIG. 25A-B.

Implementing the sensor assembly 1012 may involve several considerations. First, the coils 2502 may not be presented with an ideal open circuit. Instead, they may well be loaded by parasitic capacitance due largely to traces or conductive paths connecting the coils 2502 to the preamplifiers, as well as a damping network (described below) and an input impedance of the preamplifiers (although a low input impedance is preferred). These combined loads result in current flow when the coils 2502 link with a changing magnetic flux. Any one coil 2502, then, links magnetic flux not only from the wireless marker 40, but also from all the other coils as well. These current flows should be accounted for in downstream signal processing.

A second consideration is the capacitive loading on the coils 2502. In general, it is desirable to minimize the capacitive loading on the coils 2502. Capacitive loading forms a resonant circuit with the coils themselves, which leads to excessive voltage overshoot when the excitation source 1910 is energized. Such a voltage overshoot should be limited or attenuated with a damping or "snubbing" network across the coils 2502. A greater capacitive loading requires a lower impedance damping network, which can result in substantial power dissipation and heating in the damping network.

Another consideration is to employ preamplifiers that are low noise. The preamplification can also be radiation tolerant because one application for the sensor assembly 1912 is with radiation therapy systems that use linear accelerators (LINAC). As a result, PNP bipolar transistors and discrete elements may be preferred. Further, a DC coupled circuit may be preferred if good settling times cannot be achieved with an AC circuit or output, particularly if analog to digital converters are unable to handle wide swings in an AC output signal.

Figure 26:
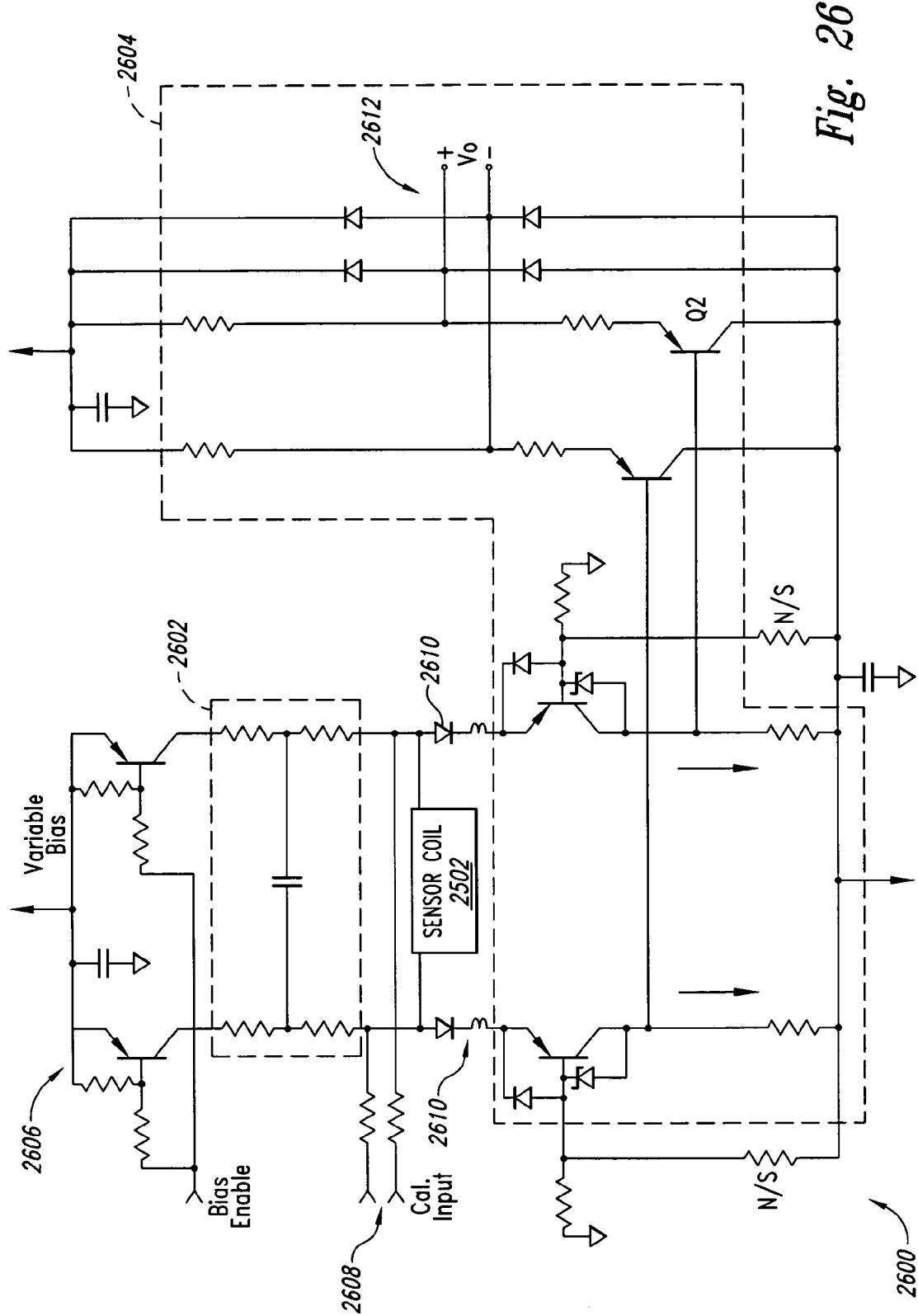
FIG. 26 is a schematic diagram of a preamplifier for use with the sensor assembly of FIG. 25A.

FIG. 26, for example, illustrates an embodiment of a snubbing network 2602 having a differential amplifier 2604. The snubbing network 2602 includes two pairs of series coupled resistors and a capacitor bridging therebetween. A biasing circuit 2606 allows for adjustment of the differential amplifier, while a calibration input 2608 allows both input legs of the differential amplifier to be balanced. The coil 2502 is coupled to an input of the differential amplifier 2604, followed by a pair of high voltage protection diodes 2610. DC offset may be adjusted by a pair of resistors coupled to bases of the input transistors for the differential amplifier 2604 (shown as having a zero value). Additional protection circuitry is provided, such as ESD protection diodes 2612 at the output, as well as filtering capacitors (shown as having a 10 nF value).

c. Signal Processors and Controllers

The signal processor 1914 and the controller 1916 illustrated in FIG. 16 receive the signals from the sensor assembly 1912 and calculate the absolute positions of the markers 40 within the reference frame. Suitable signal processing systems and algorithms are set forth in U.S. application Ser. Nos. 10/679,801; 10/749,478; 10/750,456; 10/750,164; 10/750,165; 10/749,860; and 10/750,453, all of which are incorporated herein by reference.

EXAMPLE

Overview

Figure 27:
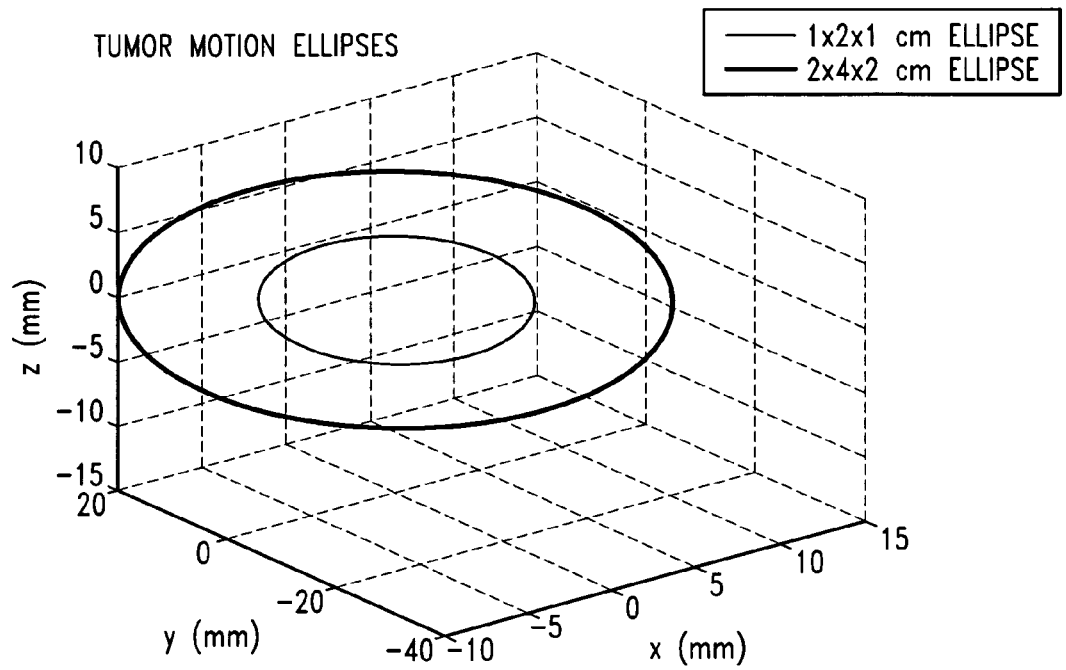
FIG. 27 is a graph of illustrative tumor motion ellipses from experimental phantom based studies of the system.

An experimental phantom based study was conducted to determine effectiveness of this system for real-time tracking. In this experiment, a custom 4D stage was constructed to allow arbitrary motion in three axes for speeds up to 10 cm/sec in each dimension, with accuracy to 0.3 mm. Position accuracy was measured by a 3D digitizing arm attached to the stage system. As shown in FIG. 27, two ellipses were created with peak to peak motion of 2 cm, 4 cm and 2 cm; and 1 cm by 2 cm and 1 cm in the x, y and z direction respectively. Three periods were used to correspond to 15, 17 and 20 breaths per minute. A single transponder was used with an integration time of 33 ms, 67 ms and 100 ms and two transponders were used with integration times of 67 ms and 100 ms. The transponders were placed in a custom phantom mounted to the 4D stage. The experiment was performed with the isocenter placed 14 cm from the AC magnetic array to simulate the position of an average lung cancer patient. The 4D stage ran each trajectory while the real time tracking system measured the transponder positions. Measured position was compared against the phantom position. The effects of ellipse size, speed, transponder number and integration time were characterized.

Experiment Summary

Figure 28:
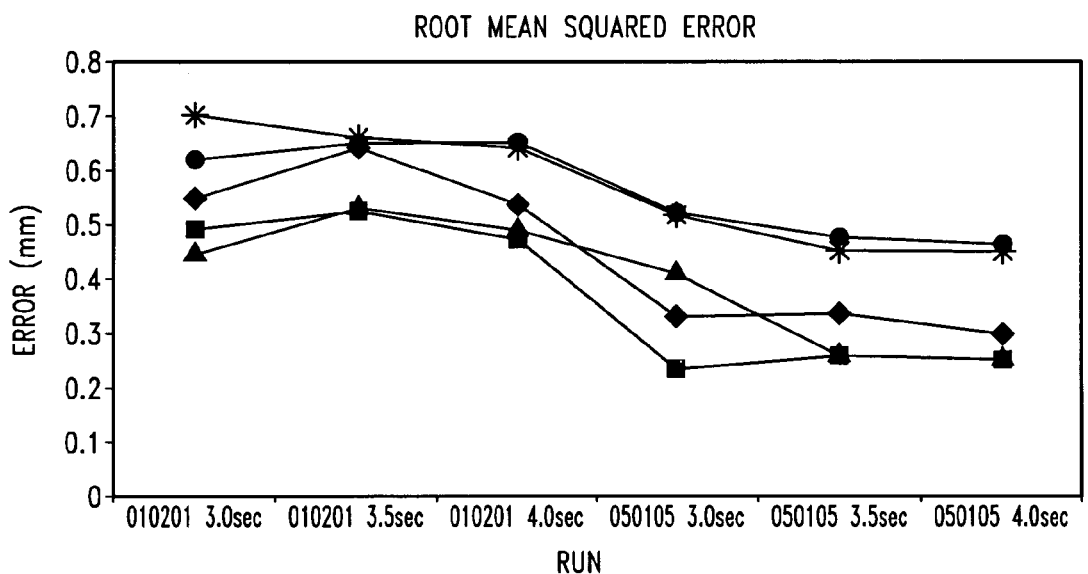
FIG. 28 is a graph of root mean square (RMS) error from experimental phantom based studies of the system.
Figure 29:
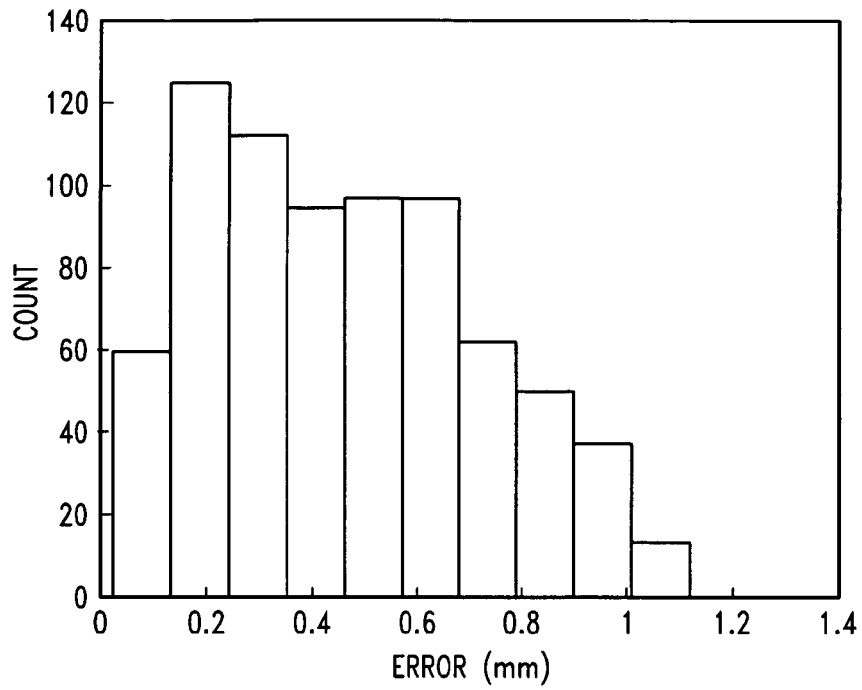
FIG. 29 is an exemplary histogram of localization error from experimental phantom based studies of the system.
Figure 30:
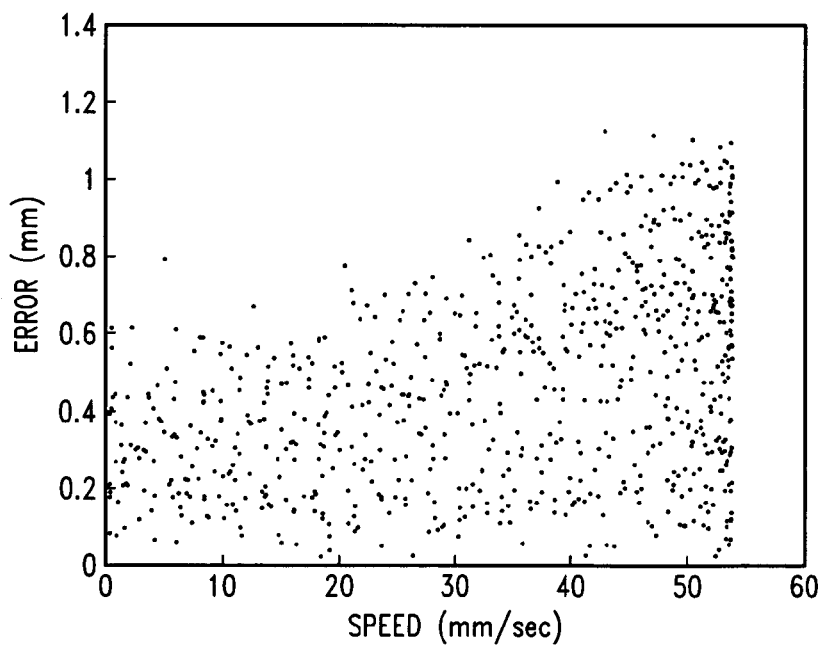
FIG. 30 is graph of position error as a function of speed from experimental phantom based studies of the system.

As shown in FIG. 28, the root mean square (RMS) error was less than 1 mm for each ellipse, period and transponder integration time. The system was able to track points throughout the path of the ellipse, for example, in a trajectory of a large ellipse moving at 17 breaths per minute. FIG. 29 is a histogram of localization errors illustrating that the range of error was low for each point measured. As shown in FIG. 30, the RMS error was higher in areas of increased velocity in most trajectories. With respect to this experiment, a single transponder system performed slightly better than dual transponder systems, with the best system being a single transponder with a 67 ms integration time.

CONCLUSION

Those skilled in the art will appreciate that the above-described facility may be straightforwardly adapted or extended in various ways. For example, the facility may operate in a wide variety of radiation treatment and treatment planning environments, and in conjunction with a wide variety of different patient tracking technologies. The facility may use a set of modules that is different from those shown and described herein. The facility may use a variety of different communication mechanisms to communicate patient position information. Patient position information may be provided to various consumers at various different levels of latency and/or frequency. In some embodiments, the facility can be used to perform patient tracking at times when the patient is not being subjected to radiation therapy treatment, such as (1) to position the patient before radiation therapy commences, or (2) to observe changes in the location, volume, shape, and/or orientation of the patient's tumor outside the radiation therapy vault. While the foregoing description makes reference to preferred embodiments, the scope of the invention is defined solely by the claims that follow and the elements recited therein.

We claim:

1. A computing system for processing data while a target is undergoing radiation therapy, comprising:
    a data receiver subsystem that is configured to cause a processor of the computing system to receive a stream of digital location indications while a patient is undergoing a continuous radiation treatment session in substantially real-time during administration of radiation treatment, each location indication identifying a location of a target in the patient using a marker secured in the patient such that the marker is substantially fixed relative to the target, the digital location indications being based upon locating the marker;
    a data processing subsystem that is configured to cause the processor of the computing system to determine whether the locations indicated by one or more location indications merits modifying a parameter of the continuous radiation treatment session, wherein the determination is in response to one or more location indications of the stream received during the continuous radiation treatment session, in substantially real-time relative to the receipt of the position indication by the data receiver subsystem;
    a modification subsystem that is configured to cause the processor of the computing system to modify the parameter during the continuous radiation treatment session in substantially real-time during administration of radiation treatment, without interrupting the continuous radiation treatment session, in response to the data processing subsystem determining that the locations indicated by one or more location indications merits modifying the parameter; and
    a data storage subsystem that is configured to cause the processor of the computing system to store the received stream of digital location indications in an electronic transcript, wherein the electronic transcript includes time-indexed information correlating the location indications received by the data receiver subsystem with treatment parameters of the continuous radiation treatment session, wherein the time-indexed information is provided as a plurality of records, and wherein each record includes:
        a measurement time at which a location indication was received by the data receiver subsystem; and
        information adequate to determine a displacement from the target to a reference point during the continuous radiation treatment session.

2. The computing system of claim 1 wherein each received location indication indicates a location occupied by the target substantially immediately before the location indication is received.

3. The computing system of claim 1 wherein each location indication indicates a location of the target in three dimensions.

4. The computing system of claim 1 wherein each location indication represents a vector from the machine isocenter point.

5. The computing system of claim 1 wherein each location indication is based upon interrogation of a plurality of passive magnetic markers attached to the target.

6. The computing system of claim 1 wherein each location indication indicates a relative location that is relative to a target location located with respect to a plurality of target-attached markers.

7. The computing system of claim 1 wherein each location indication indicates the position of a predetermined radiation treatment site of the target.

8. The computing system of claim 1 wherein each location indication indicates the location of the target relative to a location within one or more paths established for the propagation of radiation energy.

9. The computing system of claim 1 further comprising a display subsystem that is configured to cause the processor of the computing system to augment a displayed graph of locations to include the location indicated by the one or more location indications.

10. The computing system of claim 9 wherein radiation therapy is performed in a radiation therapy enclosure, and wherein the augmented graph is displayed on a device outside the radiation therapy enclosure.

11. The computing system of claim 1 wherein the electronic transcript is persistently stored.

12. The computing system of claim 1 wherein, when the locations indicated by one or more location indications merits modifying a parameter of the continuous radiation treatment session, performing a mid-treatment modification to a parameter of the continuous radiation treatment session in accordance with the locations indicated by the one or more location indications.

13. The computing system of claim 12 wherein the continuous radiation treatment session has at least one beam shape parameter specifying a cross-sectional shape of a radiation beam to be projected toward the target, and wherein the performed modification is to the beam shape parameter.

14. The computing system of claim 12 wherein the continuous radiation treatment session has a beam direction parameter specifying a direction in which a radiation beam is projected toward the target, and wherein the performed modification is to the beam direction parameter.

15. The computing system of claim 12 wherein the continuous radiation treatment session has an intensity parameter specifying a radiation intensity with which the target is to be treated, and wherein the performed modification is to the intensity parameter.

16. The computing system of claim 12 wherein the continuous radiation treatment session has at least one couch location parameter specifying a location of the couch bearing the target relative to the radiation treatment, and wherein the performed modification is to the couch location parameter.

17. The computing system of claim 12 wherein the continuous radiation treatment session has at least one couch orientation parameter specifying a orientation of the couch bearing the target relative to the radiation treatment, and wherein the performed modification is to the couch orientation parameter.

18. The computing system of claim 12 wherein the mid-treatment modification to the parameter is performed while a radiation beam is off.

19. The computing system of claim 1 wherein the the determination performed by the data processing subsystem comprises:
    comparing the location indicated by the one or more location indications with a predefined volume; and
    where the location indicated by the one or more location indications falls outside the predefined volume, presenting a warning.

20. The computing system of claim 19 wherein the warning is an audible warning.

21. The computing system of claim 19 wherein the warning is a visual warning.

22. The computing system of claim 19 wherein the warning is a redundant visual warning.

23. The computing system of claim 21 wherein the warning is displayed in a manner designed to warn a technician.

24. The computing system of claim 21 wherein the warning is displayed in a manner designed to warn the patient.

25. The computing system of claim 1 wherein the the determination performed by the data processing subsystem comprises:
comparing the location indicated by the one or more location indications with a predefined volume; and
where the location indicated by the one or more location indications falls outside the predefined volume, suspending radiation treatment in process during the receipt of the stream.

26. The computing system of claim 1 wherein the received stream of digital location indications is obtained using one or more markers attached to the target.

27. The computing system of claim 1 wherein the received stream of digital location indications is obtained using one or more markers implanted subcutaneously in the target.

28. The computing system of claim 1 wherein the received stream of digital location indications has a frequency of at least 20 hertz.

29. The computing system of claim 1 wherein the received stream of digital location indications has a latency of no more than 50 milliseconds.

30. The computing system of claim 1 wherein the received stream of digital location indications has a latency of no more than 200 milliseconds.

31. The computing system of claim 1 wherein the stream of digital location indications is received at a rate that permits the location of the marker to be tracked with an area that does not exceed a threshold of five millimeters.

32. The computing system of claim 1 wherein the determination of whether the locations indicated by one or more location indications merits modifying a parameter of the continuous radiation treatment session is performed in substantially real-time relative to a measurement time associated with performing measurements upon which the location indications are based.

33. The computing system of claim 1 wherein the parameter is a beam parameter specifying activation or termination of a radiation beam.

34. The computing system of claim 1 wherein the information adequate to determine the distance from the target to the reference point comprises:
a directed distance in a first dimension from the target to the reference point;
a directed distance in a second dimension from the target to the reference point; and
a directed distance in a third dimension from the target to the reference point.

35. The computing system of claim 1 wherein the information adequate to determine the distance from the target to the reference point comprises a relative spatial location of the target from the reference point.

36. The computing system of claim 1 wherein the reference point is a machine isocenter.

37. A non-transitory computer-readable storage medium comprising computer-executable instructions to cause a computing system to perform a method for processing data while a target is undergoing radiation therapy, the computer-executable instructions comprising:
instructions to receive a digital location indication of a target in a human patient using a marker secured in the patient such that the marker is substantially fixed relative to the target, the digital location indication being based upon locating the marker using non-ionizing radiation, wherein the digital location indication is received during a continuous radiation treatment session in substantially real-time during administration of radiation therapy;
instructions to, in response to receiving the location indication, in substantially real-time relative to the receipt of the location indication, determine whether the location indicated by the location indication merits modifying a parameter of the radiation therapy during the continuous radiation treatment session ; and
instructions to, in response to determining that the location indication merits modifying a parameter of the radiation therapy, modify the parameter of the radiation therapy during the continuous radiation treatment session in substantially real-time during administration of radiation therapy without interrupting the radiation therapy;
instructions to store the received location indication in an electronic record, wherein the electronic record includes time-indexed information correlating the received location indication with one or more treatment parameters of the radiation therapy during the continuous radiation treatment session, wherein the time-indexed information includes:
a measurement time at which the location indication was received; and
a displacement from the target to a reference point.

38. The physical computer-readable storage medium of claim 37 wherein the action is performed in substantially real-time relative to a measurement time associated with a measurement upon which the position indication is based.

39. The physical computer-readable storage medium of claim 37 wherein the location indicated by the one or more location indications merits modifying the beam parameter and a mid-treatment modification to the beam parameter is performed in accordance with the location indicated by the one or more location indications.

40. The physical computer-readable storage medium of claim 39 wherein the mid-treatment modification to the beam parameter is performed while a radiation beam corresponding to the radiation beam parameter is off.

41. The physical computer-readable storage medium of claim 37 wherein the beam parameter is a beam shape parameter specifying a cross-sectional shape of a radiation beam to be projected toward the target.

42. The physical computer-readable storage medium of claim 37 wherein the beam parameter is a beam direction parameter specifying a direction in which a radiation beam is projected toward the target.

43. The physical computer-readable storage medium of claim 37 wherein the beam parameter is a beam intensity parameter specifying a radiation intensity with which the target is to be treated.

44. The physical computer-readable storage medium of claim 37 wherein the beam parameter specifies activating or terminating a radiation beam.

45. The physical computer-readable storage medium of claim 37 wherein the beam parameter is a beam collimator parameter for controlling leaves of a multileaf collimator.

46. The physical computer-readable storage medium of claim 37 wherein the beam parameter is a modulation parameter for modulating beam intensisty.

47. The physical computer-readable storage medium of claim 37 wherein the beam parameter is a modulation parameter for controlling leaves of a multileaf collimator to effect intensity-modulated radiation therapy.

48. The physical computer-readable storage medium of claim 37 wherein the beam parameter is a beam rotation parameter specifying a rotation of a radiation beam about an axis.

49. A method in a computing system for verifying a radiation therapy session, comprising:
- using a data receiver subsystem that is configured to cause a processor of the computing system to receive a stream of digital location indications while a patient is undergoing a continuous radiation treatment session in substantially real-time during administration of radiation treatment, each location indication identifying a location of a target in the patient using a marker secured in the patient such that the marker is substantially fixed relative to the target, the digital location indications being based upon locating the marker;
- using a data processing subsystem that is configured to cause the processor of the computing system to determine whether the locations indicated by one or more location indications merits modifying a parameter of the continuous radiation treatment session, wherein the determination is in response to one or more location indications of the stream received during the continuous radiation treatment session, in substantially real-time relative to the receipt of the position indication by the data receiver subsystem;
- using a modification subsystem that is configured to cause the processor of the computing system to modify the parameter during the continuous radiation treatment session in substantially real-time during administration of radiation treatment, without interrupting the continuous radiation treatment session, in response to the data processing subsystem determining that the locations indicated by one or more location indications merits modifying the parameter;
- and a data storage subsystem that is configured to cause the processor of the computing system to store the received stream of digital location
- reading a stored set of digital location indications each identifying a location of a target while undergoing radiation therapy taken in real-time during a continuous therapy session without interrupting the radiation therapy session; and
- using the read digital location indications to review the provision of radiation therapy during the continuous therapy session, wherein reviewing the provision of radiation therapy during the continuous therapy session comprises verifying that the continuous therapy session is conducted in accordance with a continuous radiation therapy plan.

50. The method of claim 49 wherein the verification involves:
- correlating the location indications with time-indexed information about treatment parameters; and
- using the correlated information to determine that the radiation therapy was conducted in accordance with a radiation therapy plan.

51. The method of claim 49 wherein reviewing the provision of radiation therapy during the continuous therapy session comprises displaying an indication of the location of the target throughout the continuous therapy session.

52. The method of claim 49 wherein reviewing the provision of radiation therapy during the continuous therapy session comprises determining a portion of the continuous therapy session during which the target location was outside a predefined volume.

53. The method of claim 49 wherein reviewing the provision of radiation therapy during the continuous therapy session comprises identifying the smallest volume containing all of the target locations.

54. The method of claim 49, further comprising:
- reading a set of digital location indications for one or more patient-implanted markers from which the digital locations each identifying a location of the target were derived; and
- generating a revised set of digital location indications each identifying a location of the target based upon a relationship between the location of the target and the locations of the markers other than was used to generate the read set of digital location indications each identifying the location of the target.

* * * * *